United States Patent
Dobashi et al.

(10) Patent No.: US 9,902,978 B2
(45) Date of Patent: Feb. 27, 2018

(54) **GENETICALLY MODIFIED *CLOSTRIDIUM SACCHAROPERBUTYLACETONICUM***

(71) Applicant: NIPPON SHOKUBAI CO., LTD., Osaka (JP)

(72) Inventors: Yukio Dobashi, Tsukuba (JP); Masaharu Mukoyama, Tsukuba (JP); Eita Ichige, Tsukuba (JP); Masahiro Nakanosho, Tsukuba (JP); Shunichi Nakayama, Tokyo (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 0 days.

(21) Appl. No.: 14/779,801

(22) PCT Filed: Feb. 28, 2014

(86) PCT No.: PCT/JP2014/055140
§ 371 (c)(1),
(2) Date: Sep. 24, 2015

(87) PCT Pub. No.: WO2014/156476
PCT Pub. Date: Oct. 2, 2014

(65) Prior Publication Data
US 2016/0053285 A1    Feb. 25, 2016

(30) Foreign Application Priority Data

Mar. 26, 2013 (JP) .................................. 2013-063347
Feb. 24, 2014 (JP) .................................. 2014-032953

(51) Int. Cl.
| | |
|---|---|
| *C12P 7/16* | (2006.01) |
| *C12N 1/21* | (2006.01) |
| *C12N 15/52* | (2006.01) |
| *C12N 1/20* | (2006.01) |

(52) U.S. Cl.
CPC ............... *C12P 7/16* (2013.01); *C12N 1/20* (2013.01); *C12N 15/52* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 2010/0086982 A1* | 4/2010 | Soucaille | .................. | C12P 7/16 435/160 |
| 2011/0296747 A1 | 12/2011 | Sonomoto et al. | | |

FOREIGN PATENT DOCUMENTS

| | | | |
|---|---|---|---|
| CN | 101519673 A | 9/2009 | |
| JP | 2010-508017 A | 3/2010 | |
| WO | 2008/052596 A1 | 5/2008 | |
| WO | 2008/052973 A2 | 5/2008 | |
| WO | 2011/099165 A1 | 8/2011 | |
| WO | WO 2013128230 A1 * | 9/2013 | ................ C12P 7/16 |

OTHER PUBLICATIONS

Cerro et al., Genome Announce. 1:e00070-13, 2 pages, Mar. 7, 2013.*
Cary et al., J. Bacteriol. 170:4613-4618, 1988.*
Boynton et al., Appl. Environ. Microbiol. 62:2758-2766, 1996.*
Green et al., "Genetic manipulation of acid formation pathways by gene inactivation in Clostridium acetobutylicum ATCC 824," Microbiology, 1996, vol. 142, pp. 2079-2086.
Cooksley et al., "Targeted mutagenesis of the Clostridium acetobutylicum acetone-butanol-ethanol fermentation pathway," Metabolic Engineering, vol. 14, 2012, pp. 630-641.
Nair et al., "Molecular characterization of an aldegyde/alcohol degydrogenase gene from Clostridium acetobutylicum ATCC 824," Journal of Bacteriology, Feb. 1994, pp. 871-885.
Sillers et al., "Aldegyde-Alcohol dehydrogenase and/or thiolase overexpression coupled with CoA transferase downregulation lead to higher alcohol titers and selectivity in Clostridium acetobutylicum fermentations," Biotechnology and Bioengineering, vol. 102, No. 1, Jan. 1, 2009, pp. 38-49.
Lehmann et al., "Modifying the product pattern of Clostridium acetobutylicum," Appl. Microbiol. Biotechnol., 2012, vol. 94, pp. 743-754.
Jang et al., "Enhanced butanol production obtained by reinforcing the direct butanol-forming route in Clostridium acetobutylicum," mBio 3:e00314-12, 9 pages, 2012.
PCT International Search Report dated May 27, 2014, which was issued in related PCT International Application No. PCT/JP2014/055140 (3 pgs.).
Japanese Office Action issued for Japanese Patent Application No. 2014-032953, dated Sep. 19, 2017 (6 pages).

* cited by examiner

*Primary Examiner* — David Steadman
(74) *Attorney, Agent, or Firm* — Lucas & Mercanti, LLP

(57) ABSTRACT

The present invention provides a means for producing butanol in butanol fermentation with high efficiency. The present invention relates to a genetically modified microorganism of *Clostridium saccharoperbutylacetonicum*, and a method for producing butanol using the microorganism.

7 Claims, 6 Drawing Sheets

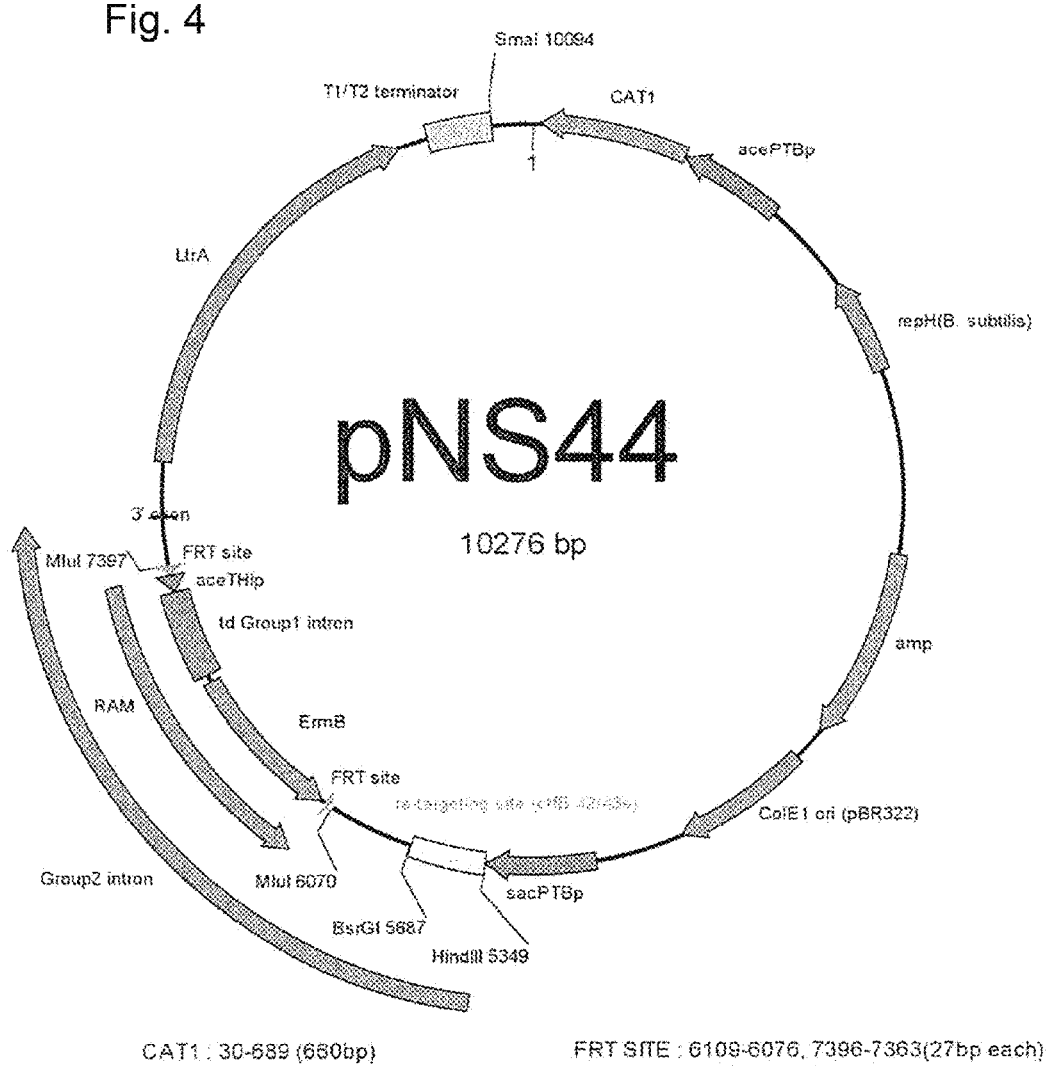

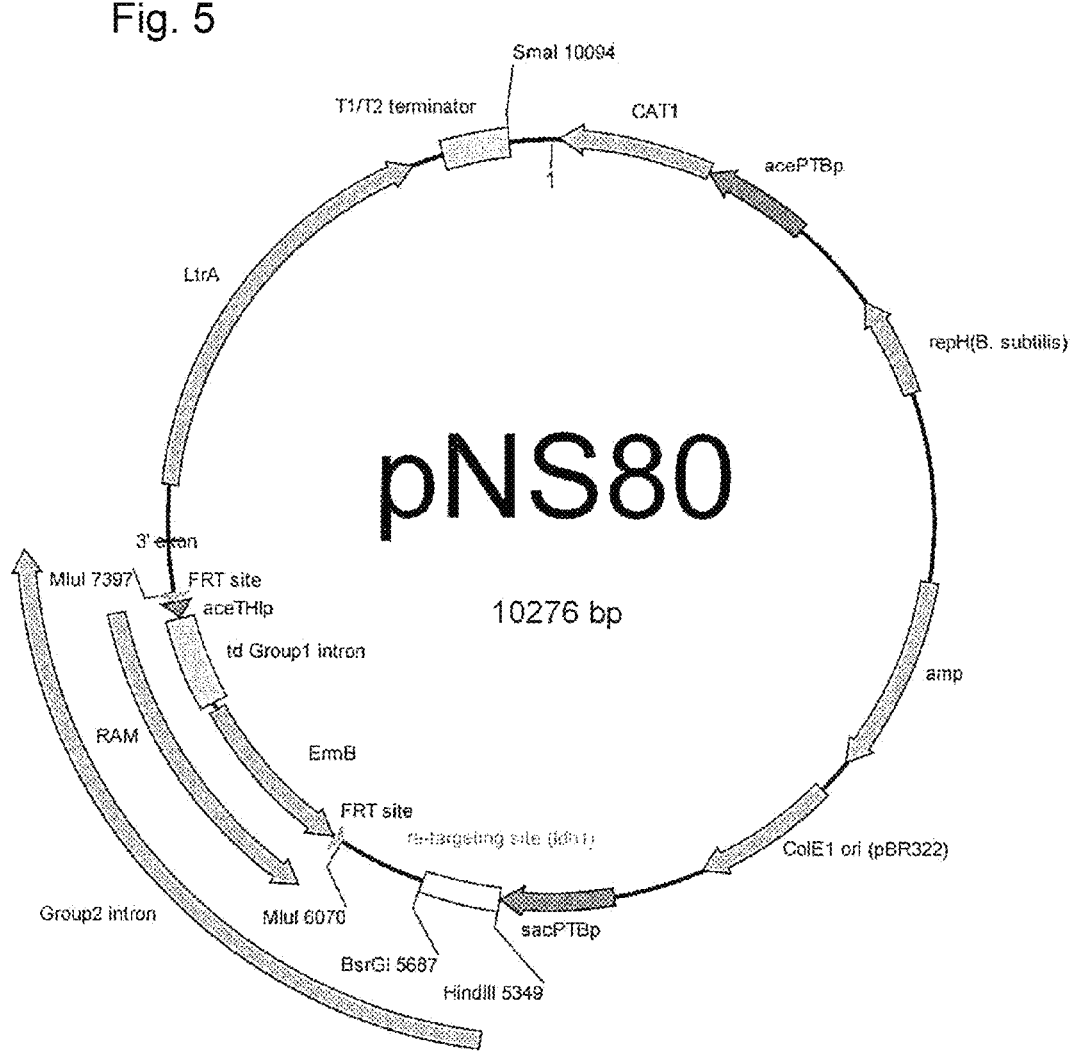

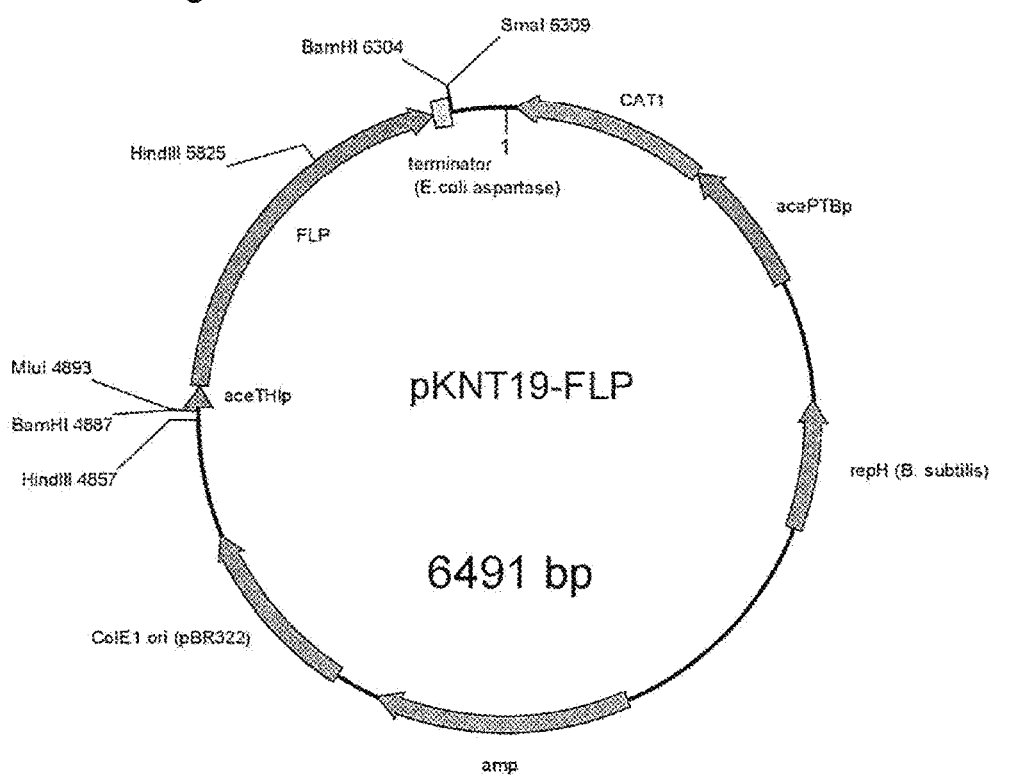

GENETICALLY MODIFIED CLOSTRIDIUM SACCHAROPERBUTYLACETONICUM

CROSS-REFERENCE TO RELATED APPLICATIONS

This application is a 371 of PCT/JP2014/055140, filed Feb. 28, 2014, which claims the benefit of Japanese Patent Application Nos. 2013-063347, filed Mar. 26, 2013 and 2014-032953, filed Feb. 24, 2014.

TECHNICAL FIELD

The present invention relates to a genetically modified microorganism of *Clostridium saccharoperbutylacetonicum* and a method for producing butanol using the microorganism.

BACKGROUND ART

In microorganic butanol fermentation, solvents such as acetone and ethanol and organic acids such as butyric acid, acetic acid and lactic acid are produced as by-products in addition to butanol. These by-products are a factor of lowering butanol yield and an obstacle in constructing a process for collecting butanol.

In butanol fermentation, decreasing by-products (e.g., acetone, ethanol, organic acids) is very useful for improving the yield of butanol in relation to glucose and simplifying a separation/purification step. In the circumstances, studies for decreasing by-products have been made. As a method therefor, disruption of by-product synthetic genes or enhancement of butanol synthetic genes have been frequently adopted and carried out by means using homologous recombination and mutation. For example, in Non Patent Literature 1, a buk (butyrate kinase) gene and a pta (phosphotransacetylase) gene are disrupted by homologous recombination. However, in this method, acetic acid production increases significantly when the butyric acid production pathway is disrupted and butyric acid production increases significantly when the acetic acid production pathway is disrupted. In addition, there is a case where production of a solvent increases as in the case where aad (alcohol/aldehyde dehydrogenase) gene is cloned and thereafter excessively expressed (Non Patent Literature 2). There is another case where gene suppression and introduction are simultaneously performed. In Non Patent Literature 3, thl (acetyl-CoA dimerized enzyme) gene and aad gene are expressed while expression of ctfB (subunit B of CoA transferase) gene is suppressed thereby the concentration of ethanol is increased to about 13 g/L.

As a case in which ethanol and butanol are produced without producing acetone, Non Patent Literature 4 discloses simultaneous disruption of adc (acetoacetate decarboxylase) gene or ctfAB (CoA transferase) gene and pta gene. In that case, butyric acid accumulates significantly whereas production of butanol decreases drastically. Patent Literature 1 describes that a strain in which buk or ptb (phosphotransbutyrylase) gene of *Clostridium acetobutyricum* is disrupted such that butyric acid production pathway is disrupted is further subjected to adjustment of acetone, lactic acid, acetic acid and hydrogenase production. However, specific numerical values thereof are not disclosed in the literature. In Non Patent Literature 5, ptb and pta genes and buk and pta genes are disrupted in *Clostridium acetobutyricum*; however, a decreasing effect in production of by-products including butyric acid and acetic acid is not sufficient and an increase in butanol yield has not been achieved.

Accordingly, it has been desired to develop a microorganism capable of producing butanol with high efficiency while suppressing production of by-products such as butyric acid, acetic acid and ethanol.

CITATION LIST

Patent Literature

Patent Literature 1: WO 2008/052596

Non Patent Literature

Non Patent Literature 1: Green et al., Microbiology., 142: 2079, 1996
Non Patent Literature 2: Nair et al., J. Bacteriol., 176: 871, 1994
Non Patent Literature 3: Sillers et al., Biotechnol Bioeng., 102: 38, 2009
Non Patent Literature 4: Lehmann et al., Appl Microbiol Biotechnol., 94: 743, 2012
Non Patent Literature 5: Jang et al., mbio 2012., 23: 00314, 2012

SUMMARY OF INVENTION

Technical Problem

An object of the present invention is to improve the yield of butanol in butanol fermentation by suppressing production of by-products other than butanol.

Solution to Problem

The present inventors succeeded in improving butanol yield by disrupting the pathway leading to production of butyric acid from butyryl-CoA in a microorganism of *Clostridium saccharoperbutylacetonicum* thereby suppressing production of not only butyric acid but also other by-products in butanol fermentation using the microorganism, and arrived at the present invention.

More specifically, the present invention encompasses the following.

(1) A microorganism of *Clostridium saccharoperbutylacetonicum* wherein a function of a butyric acid producing enzyme gene involved in a pathway leading to production of butyric acid from butyryl-CoA is disrupted.

(2) The microorganism according to (1), in which the functions of ptb and/or buk as the butyric acid producing enzyme gene are disrupted.

(3) The microorganism according to (1) or (2), in which a function of an acetic acid producing enzyme gene involved in a pathway leading to production of acetic acid from acetyl-CoA is further disrupted.

(4) The microorganism according to (3), in which the functions of pta and/or ack as the acetic acid producing enzyme gene are disrupted.

(5) The microorganism according to any of (1) to (4), in which a function of an acetone producing enzyme gene involved in a pathway leading to production of acetone from acetoacetyl-CoA is further disrupted.

(6) The microorganism according to (5), in which the functions of adc and/or ctfAB as the acetone producing enzyme gene are disrupted.

(7) The microorganism according to any of (1) to (6), in which a function of a lactic acid producing enzyme gene involved in a pathway leading to production of lactic acid from pyruvic acid is further disrupted.

(8) The microorganism according to (7), in which the function of ldh1 as the lactic acid producing enzyme gene is disrupted.

(9) A method for producing butanol, comprising a step of culturing the microorganism according to any of (1) to (8) in a medium containing a carbon source.

(10) The method according to (9), comprising a step of collecting butanol from a culture solution.

Advantageous Effects of Invention

According to the present invention, improvement in butanol yield in butanol fermentation and simplification of separation/purification of butanol from fermentation liquor are achieved, and thereby economically advantageous production of butanol is realized.

This specification incorporates the content of the specification and/or drawings of Japanese Patent Applications Nos. 2013-063347 and 2014-032953, from which priority is claimed to the present application.

BRIEF DESCRIPTION OF DRAWINGS

FIG. 4 shows a plasmid map of pNS44 plasmid.
FIG. 5 shows a plasmid map of pNS80 plasmid.
FIG. 6 shows a plasmid map of pKNT19-FLP plasmid.

DESCRIPTION OF EMBODIMENTS

Figure 1:
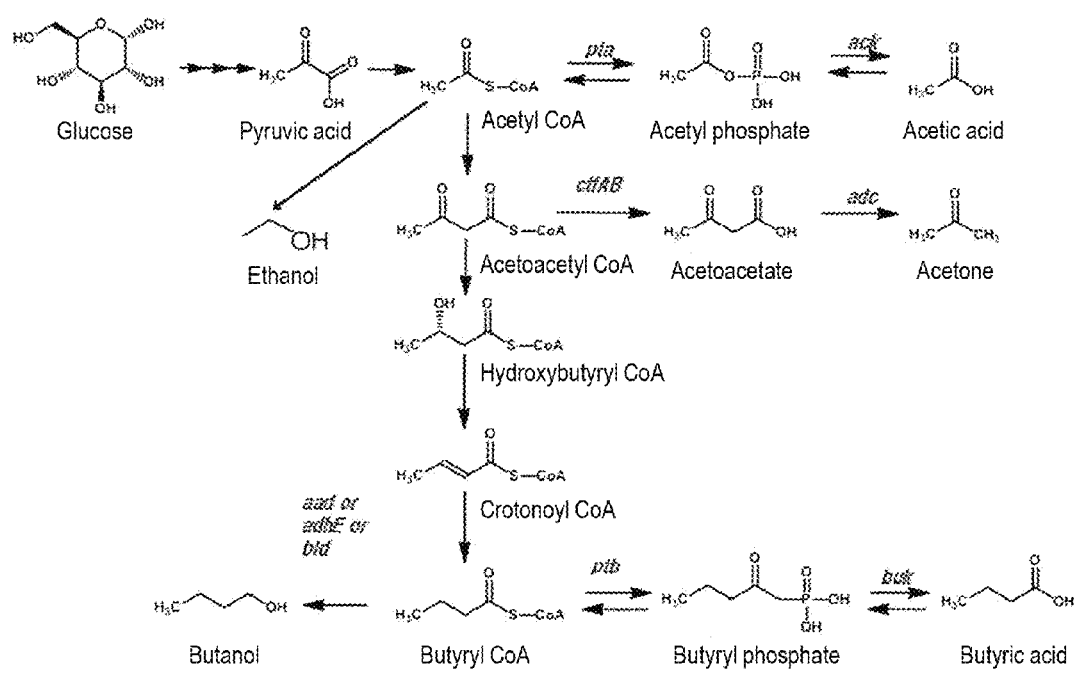
FIG. 1 illustrates a metabolic pathway of butanol fermentation together with intermediate compounds and enzyme genes involved therein.

The microorganism of the present invention can be obtained by disrupting a function of butyric acid producing enzyme gene in *Clostridium saccharoperbutylacetonicum* (*C. saccharoperbutylacetonicum*). *C. saccharoperbutylacetonicum* has a butanol production ability. Specific examples of the strain include, but not particularly limited to, ATCC27021 strain and ATCC13564 strain.

Though introduction of a plasmid to microorganisms of *Clostridium* genus is difficult, introduction of a plasmid to *C. saccharoperbutylacetonicum* can be made with comparative ease. In the case of *C. acetobutyricum* ATCC824 strain and the like, for example, a plasmid cannot be introduced as it is and a methylation treatment must be performed since the plasmid is cleaved by DNA endonuclease. However, *C. saccharoperbutylacetonicum* does not require such treatment.

The butyric acid producing enzyme gene is a gene encoding an enzyme involved in the pathway leading to production of butyric acid from butyryl-CoA. Examples of the butyric acid producing enzyme gene include ptb gene (gene encoding phosphotransbutyrylase) and buk gene (gene encoding butyrate kinase). Phosphotransbutyrylase is an enzyme catalyzing a reaction of producing butyryl phosphate from butyryl-CoA. Butyrate kinase is an enzyme catalyzing a reaction of converting butyryl phosphate to butyric acid. Disruption of a function of butyric acid producing enzyme gene includes disruption of the function of one of these genes and disruption of the functions of two or more of these genes as well as disruption of one or more functions of genes encoding an enzyme subunit.

The examples where the butyric acid production pathway is disrupted include Non Patent Literature 1, Patent Literature 1 and Non Patent Literature 5. In Non Patent Literature 1, however, a large amount of acetic acid is produced by the disruption of the butyric acid production pathway and the yield of butanol is not improved. Patent Literature 1 describes a disrupted strain but does not describe culture results thereof. Though Non Patent Literature 5 describes the results of disruption of production pathways of both acetic acid and butyric acid, no improvement of butanol yield was obtained unless alcohol dehydrogenase expression is externally performed. These studies are all performed on *C. acetobutyricum*.

The bacterial strain used in the present application is *C. saccharoperbutylacetonicum*. Surprisingly, even if the butyric acid production pathway is disrupted in the strain, a phenomenon as observed in *C. acetobutyricum*, i.e., increase in acetic acid, was not observed and growth of the bacterial cells was satisfactory and butanol yield was increased.

As described above, it was found that, in contrast to that disruption of the butyric acid production pathway has no significant effect upon butanol production in *C. acetobutyricum*; in *C. saccharoperbutylacetonicum*, disruption of the butyric acid production pathway has an effect of reducing by-products and improving butanol yield. It was also found that when the acetic acid production pathway of the strain whose butyric acid production pathway was already disrupted is further disrupted, productions of acetic acid and butyric acid are drastically reduced and butanol yield is drastically improved.

In the microorganism of the present invention, it is preferable that the function of acetic acid producing enzyme gene is disrupted. By disrupting the function, the butanol yield in butanol fermentation can be further improved.

The acetic acid producing enzyme gene is a gene encoding an enzyme involved in the pathway leading to production of acetic acid from acetyl-CoA. Examples of the acetic acid producing enzyme gene include pta gene (gene encoding phosphotransacetylase) and ack gene (gene encoding acetate kinase). Phosphotransacetylase is an enzyme catalyzing a reaction of producing acetyl phosphate from acetyl-CoA. Acetate kinase is an enzyme catalyzing a reaction of converting acetyl phosphate to acetic acid. Disruption of the function of acetic acid producing enzyme gene includes disruption of the function of one of these genes and disruption of the functions of two or more of these genes as well as disruption of one or more functions of genes encoding an enzyme subunit.

In the microorganism of the present invention, the function of acetone producing enzyme gene may further be disrupted. By disrupting the acetone producing enzyme gene, acetone as a by-product is not produced and a separation/purification step is more simplified. Further improvement in yield is expected by combining with a technique of culture using reducing power supply.

The acetone producing enzyme gene is a gene encoding an enzyme involved in the pathway leading to production of acetone from acetoacetyl-CoA. Examples of the acetone producing enzyme gene include ctfA gene (gene encoding subunit A of CoA transferase), ctfB gene (gene encoding subunit B of CoA transferase) and adc gene (gene encoding acetoacetate decarboxylase). CoA transferase, which contains subunit A and subunit B, catalyzes a reaction of converting acetoacetyl-CoA to acetoacetate. The notation of ctfAB refers to both of a gene encoding subunit A and a gene encoding subunit B of CoA transferase. Acetoacetate decarboxylase is an enzyme catalyzing a reaction of producing acetone by decarboxylating acetoacetate. Disruption of the function of the acetone producing enzyme gene includes disruption of the function of one of these genes and disruption of the functions of two or more of these genes as well as disruption of one or more functions of genes encoding an enzyme subunit.

In the microorganism of the present invention, the function of lactic acid producing enzyme gene may further be disrupted. By disrupting the lactic acid producing enzyme gene, lactic acid as a by-product is not produced and a separation/purification step is more simplified. In addition, since reducing power can further be used in butanol production, a further improvement in yield can be expected.

A lactic acid producing enzyme gene is a gene encoding an enzyme involved in the pathway leading to production of lactic acid from pyruvic acid. Lactate dehydrogenase is encompassed in the lactic acid producing enzyme gene. Lactate dehydrogenase is an enzyme catalyzing interconversion between lactic acid and pyruvic acid. At the same time, interconversion between NADH and $NAD^+$ occurs simultaneously. There are four different types of lactate dehydrogenases. Two of them are cytochrome c-dependent types, which act on D-lactic acid (D-lactate dehydrogenase: EC1.1.2.4) or L-lactic acid (L-lactate dehydrogenase: EC1.1.2.3), respectively. The remaining two types are NAD(P)-dependent enzymes, which act on D-lactic acid (D-lactate dehydrogenase: EC1.1.1.28) or L-lactic acid (L-lactate dehydrogenase: EC1.1.1.27), respectively. Specific examples of the lactate dehydrogenase include ldh1, ldh2, lldD and ldh3. In particular, disruption of the function of ldh1 is preferable. Disruption of the function of lactic acid producing enzyme gene includes disruption of the function of one of these genes and disruption of the functions of two or more of these genes.

In the present invention, a gene includes DNA and RNA, and DNA includes single stranded DNA and double stranded DNA.

Disruption of a function of enzyme gene encompasses partial or whole modification (e.g., substitution, deletion, addition and/or insertion) or disruption of an enzyme gene such that the expression product of the gene loses a function as the enzyme and an enzyme protein is not expressed. For example, a function of enzyme gene can be completely or substantially dysfunctional or disrupted by causing a deletion, substitution, addition or insertion in a part of genomic DNA of the enzyme gene. A partial or whole modification (e.g., substitution, deletion, addition and/or insertion) or disruption of a promoter of enzyme gene is also encompassed. Herein, disruption of a gene refers to the state where the function of the enzyme gene is completely or substantially dysfunctional by deleting a part or whole of the gene sequence; by inserting another DNA sequence in the gene sequence; or by substituting a part of its gene sequence with another sequence.

In the present invention, a transformant of *Clostridium saccharoperbutylacetonicum*, in which functions of enzyme genes are disrupted, is a knockout microorganism in which the functions of enzyme genes on the genome are disrupted. Such a transformant can be prepared generally by using a gene targeting recombination method (gene targeting method: for example, Methods in Enzymology 225: 803-890, 1993) known in the art, for example, by homologous recombination. The homologous recombination method can be performed by inserting a target DNA into the sequence homologous to the sequence on the genome, introducing the DNA fragment into a cell, and allowing the cell to cause homologous recombination. In the introducing into the genome, a strain in which homologous recombination took place can be easily screened by using a DNA fragment in which a target DNA is ligated to a drug resistant gene. Alternatively, it is also possible to insert a DNA fragment in which a drug resistant gene is ligated to a gene to be lethal under specific conditions by homologous recombination thereafter substituting the drug resistant gene with the gene to be lethal under specific conditions. Furthermore, a method using group II intron found in *lactobacillus* (Guo et. al., Science 21; 289 (5478): 452-7 (2000)) and a genome processing method such as TALEN technology and CRISPR technology can be used.

Group II intron is an intron having a function of forming a complex with a protein of *lactobacillus* called LtrA and being inserted into a specific region of a genome. By modifying the site of the intron called as a targeting region appropriately, the DNA sequence can be inserted into a desired site of a microorganism genome. If the site at which the DNA is inserted is within a gene, the gene almost loses its function in most cases. This method can be used as a means for disrupting a gene. By inserting an appropriate drug resistant gene within group II intron and inserting within the drug resistant gene a self-splicing DNA region called td intron, the drug resistant gene cannot be expressed in the state of a vector while the drug resistant gene comes to act when the drug resistant gene takes a form of the group II intron and DNA sequence is inserted with the td intron self-spliced. The gene-disrupted strain obtained in this manner can be easily screened by using drug resistance acquired by the drug resistant gene introduced in the genome as a marker.

The site called as a targeting sequence has been analyzed by using *Escherichia coli* by Perutka et al. (Perutka et al., J. Mol. Biol. 13; 336 (2): 421-39 (2004)). As a result, it became possible to predict which site of a sequence is modified in which way to insert the sequence to a target DNA sequence. For example, by programming excel macro and entering the nucleotide sequence of a target gene that is wished to be disrupted to the macro based on the literature, the DNA insertion site of the target gene and a method of modifying a targeting sequence can be output.

In general, when a drug resistant gene is used for screening a gene disrupted strain, another drug resistant gene is required for disrupting multiples of genes. However, if a drug resistant gene is spliced out by use of e.g., the FLP-FRT method (Schweizer H P, J. Mol. Microbiol. Biotechnol. 5 (2): 67-77 (2003)) or the Cre-loxP method (Hoess et al., Nucleic Acids Res. 11; 14 (5): 2287-300 (1986)), drug resistance can be overcome. FLP and Cre recognize a short DNA sequence consisting of about 25 bases called FRT and loxP, respectively, and have a function of cutting out the region sandwiched between FRTs or loxPs. More specifically, a gene disrupted strain having drug sensitivity can be obtained by conducting a gene disruption using a gene-disruption vector in which an FRT sequence or a loxP sequence is arranged on the side part of a drug resistant gene and thereafter introducing an another vector in which FLP or Cre gene is cloned to the obtained gene disrupted strain having drug resistance and allowing to act thereto. Thereafter, gene disruption can be carried out again in the same manner as mentioned above.

As DNA sequences encoding a butyric acid producing enzyme gene, an acetic acid producing enzyme gene, an acetone producing enzyme gene and a lactic acid producing enzyme gene, sequences known to the public registered in the GenBank may be used. The nucleotide sequences of ctfA, ctfB and adc of *C. saccharoperbutylacetonicum* ATCC13564 strain are registered under Accession Number AY251646. With respect to ATCC27021 strain used herein, the nucleotide sequences of ptb is shown as SEQ ID NO: 1; the base sequence of pta is shown as SEQ ID NO: 2; the base sequence of ctfB is shown as SEQ ID NO: 3; and the base sequence of ldh1 is shown as SEQ ID NO: 8.

Genes functionally equivalent to the enzyme genes encoded by the above nucleotide sequences are also encompassed in the enzyme genes. Genes functionally equivalent to an enzyme gene consisting of a certain nucleotide sequence include genes consisting of a sequence having 70% or more, preferably 80% or more, more preferably 90% or more, further preferably 95% or more, and most preferably 99% or more of homology (or identity) to said nucleotide sequence and encoding a protein having the same enzymatic activity. For example, as the gene functionally equivalent to ptb consisting of the sequence represented by SEQ ID NO: 1, genes consisting of a nucleotide sequence having 70% or more, preferably 80% or more, more preferably 90% or more, further preferably 95% or more, and most preferably 99% or more of homology (or identity) to the nucleotide sequence represented by SEQ ID NO: 1 and encoding a protein having phosphotransbutyrylase activity can be exemplified. In addition, those skilled in the art can determine equivalent genes in other microorganisms with reference to the reference numbers given to known genes by the GenBank.

A probe (for example, about 30 to 150 bases) prepared based on a known sequence, tagged with a radioactive or fluorescent label can be used for detecting or isolating genomic DNA of each enzyme gene. The open-reading frame (ORF) of a desired enzyme gene can be searched with using the above prove by extracting DNA from microorganism cells in a conventional manner, cleaving with restriction enzymes, and subjecting to hybridization such as Southern hybridization and in-situ hybridization. A targeting vector is designed by preparing a restriction enzyme map as necessary and determining an arbitrary target site for homologous recombination.

A vector for preparing a targeting vector by inserting a recombinant DNA is not particularly limited as long as it is replicable in a microorganism of *Clostridium* genus. It is favorable if the vector is a shuttle vector of *Escherichia coli* and a microorganism of *Clostridium* genus and particularly preference is given to a shuttle vector pKNT19 derived from pIM13 (Journal of General Microbiology, 138, 1371-1378 (1992)).

A vector for obtaining a strain having a disrupted gene by transformation can be obtained by cloning a necessary sequence from a microorganic genomic DNA as a template or synthesizing and, if necessary, ligating sequences appropriately to provide the necessary sequence. A method for obtaining a desired gene or a promoter from microorganic genomic DNA by cloning is commonly known in the art of molecular biology. For example, in the case where the gene sequence is known, an appropriate genomic library can be prepared by restriction endonuclease digestion and a desired gene can be screened by use of a complementary probe to the desired gene. After the sequence is isolated, an amount of DNA suitable for transformation can be obtained by amplifying the DNA using a standard amplification method such as a polymerase chain reaction (PCR) (U.S. Pat. No. 4,683,202). Sambrook, J., Fritsch, E. F., Maniatis, T., Molecular Cloning, Cold Spring Harbor Laboratory Press, 1.21 (1989) discloses methods of preparation of a genomic DNA library used for cloning, hybridization, PCR, preparation of plasmid DNA, cleavage and ligation of DNA, transformation and the like. A DNA sequence can be directly synthesized. Alternatively, a DNA sequence having a longer chain can be obtained via ligation by subjecting the DNA sequence obtained via PCR and the like to a treatment with restriction enzymes and conducting ligation, or conducting PCR reaction with using a sequence in which a probe (primer) complementary to the both ends of the DNA sequence is ligated to a 15 bp length homologous region of another DNA sequence and thereafter ligating by conducting an infusion reaction (U.S. Pat. No. 7,575,860).

Introduction of a targeting vector to a microorganism can be carried out by a method known to the public. Examples of the introduction method include, but not particularly limited to, a microcell method, a calcium phosphate method, a liposome method, a protoplast method, a DEAE-dextran method and an electroporation method. An electroporation method is preferably used.

The obtained transformant is cultured in a medium for butanol production to yield butanol by butanol fermentation. As the medium and culture conditions to be used for culturing, those known in the field of butanol fermentation can be used. The culture medium usually contains a carbon source, a nitrogen source and inorganic ions.

As the carbon source, preferably sugars such as monosaccharides, oligosaccharides and polysaccharides are used. Preference is given to monosaccharides, particularly to glucose. In combination with glucose, other sugars such as lactose, galactose, fructose and starch hydrolysate, alcohols such as sorbitol, or organic acids such as fumaric acid, citric acid and succinic acid may be used.

As the nitrogen source, for example, inorganic ammonium salts such as ammonium sulfate, ammonium chloride and ammonium phosphate, organic nitrogen compounds such as soybean hydrolysate, ammonia gas, ammonium solution and the like can be used.

As the inorganic ion, potassium phosphate, magnesium sulfate, an iron ion, a manganese ion and the like are added. As the organic micronutrient, required substances such as thiamine, p-aminobenzoic acid, vitamin B1 and biotin and yeast extract and the like may be desirably added in an appropriate amount, as needed.

In the present invention, by culturing the transformant preferably in the condition where a reducing power is increased, butanol can be highly efficiently produced while suppressing production of by-products such as acetone, ethanol, acetic acid, butyric acid and lactic acid. An absolute amount of butanol produced can also be increased. The culture in the condition where a reducing power is increased means that an enzyme reaction taking place during culturing is performed in the conditions where a reducing power is increased. The reducing power can be increased by adding, for example, NADH, by introducing hydrogen or by increasing hydrogen partial pressure within a culture vessel. By increasing hydrogen partial pressure within a culture vessel, it is considered that the hydrogen partial pressure of a gas phase in contact with a culture solution increases and hydrogen in the gas phase in contact with the culture solution is immediately taken by hydrogenase.

The hydrogen partial pressure in a culture vessel can be increased, for example, by performing culture in a closed state. In the closed state, external release of hydrogen from microorganisms is limited and thereby hydrogen partial pressure in a culture vessel can be increased. Alternatively, hydrogen may be introduced from the outside. For example, hydrogen may be introduced to a culture solution by bubbling or to a gas-phase portion of a culture vessel, or may also be introduced so as to be in contact with a culture solution. More specifically, the hydrogen partial pressure in a culture vessel in the range of 20 to 40° C. is preferably 0.06 atm or more, more preferably 0.08 atm or more, further preferably 0.10 atm or more, further more preferably 0.12 atm or more, most preferably 0.15 atm or more and preferably 10 atm or less.

Hydrogen partial pressure can be measured by a method known to the public and the measurement method is not particularly limited. For example, the hydrogen partial pressure can be measured by trapping the gas generated in an aluminum bag, determining hydrogen concentration of the gas in the bag by gas chromatography, quantifying the amount of hydrogen generated by multiplying the concentration and the volume, and calculating from the amount of hydrogen generated and the volume of the gas-phase portion in a culture vessel.

In the present invention, production amount of butanol relative to by-products can be improved by performing culture under pH control. The pH of the medium is controlled, if necessary, so as to be preferably 4.6 or more, 4.7 or more, 4.8 or more, 4.9 or more, 5 or more or 5.5 or more, preferably 8 or less, 7.5 or less, 7.0 or less, 6.9 or less, 6.8 or less, 6.7 or less, 6.6 or less or 6.5 or less. To control pH, inorganic or organic substances that are acidic or alkalic such as calcium carbonate, ammonia, sodium hydroxide, potassium hydroxide, potassium phosphate and the like can be used. The pH control encompasses the case where the pH of a culture medium is kept to the target pH without adding alkalic substances as above. For example, in the case where ammonium sulfate is used as a nitrogen source, decrease in pH may be suppressed and growth may be improved by replacing it with ammonium acetate having a high buffer capacity.

Other culture conditions are not particularly limited and conditions conventionally used in the technical field can be employed. For example, when a batch culture is performed, the culture time is usually 5 to 100 hours and preferably 12 to 48 hours. When a continuous culture or feeding culture is performed, the culture time is usually 200 hours or more, preferably 500 hours or more and more preferably 1000 hours or more. The culture temperature is usually 20 to 55° C. and preferably 25 to 40° C. and is controlled to about 30° C. for example.

In the producing method of the present invention, the production ratio of butanol relative to by-products, which is a numerical value obtained by dividing the molar number of the butanol generated by the total molar number of the acetone, ethanol, acetic acid and butyric acid generated, is preferably 2.5 or more, 3.0 or more, 4.0 or more or 5.0 or more.

Furthermore, the production ratio of butanol relative to by-products, which is a numerical value obtained by dividing the molar number of butanol generated by the total molar number of acetone, ethanol, acetic acid, butyric acid and lactic acid generated, is preferably 2.5 or more, 3.0 or more, 4.0 or more or 5.0 or more.

Collection of a fermentation product, i.e., butanol, from culture solution of during or after completion of culture can be carried out by a method known to the public without using any special method. Collection can be made during or after completion of culture by combining methods known in the technical field such as distillation, gas stripping, solvent extraction and other methods. Preferably, butanol is collected during culture by gas stripping or solvent extraction followed by purified via distillation. In the method of the present invention, since production amount of butanol relative to production amount of by-products is large and therefore the yield of butanol is high and separation/purification step of butanol can be simplified, the method of the present invention is advantageous in terms of cost.

Hereinafter, the present invention will be more specifically described by way of examples; however, the scope of the present invention is not limited to the examples.

EXAMPLES

Example 1

Preparation of Transformed Microorganism

Based on Perutka et al., J. Mol. Biol. 13; 336 (2): 421-39 (2004), an excel macro which outputs an insertion site of group II intron and a modification method of targeting sequence in a target gene by entering nucleotide sequence of the target gene was programmed. Then, the nucleotide sequences of a ptb gene, a pta gene, a ctfB gene and a ldh1 gene to be subjected to gene disruption were entered in the macro so as to output modification sites of the targeting sequence. The nucleotide sequence of the ptb gene is shown as SEQ ID NO: 1; the nucleotide sequence of the pta gene is shown as SEQ ID NO: 2; the nucleotide sequence of the ctfB gene is shown as SEQ ID NO: 3; and the nucleotide sequence of ldh1 gene is shown as SEQ ID NO: 8.

Figure 2:
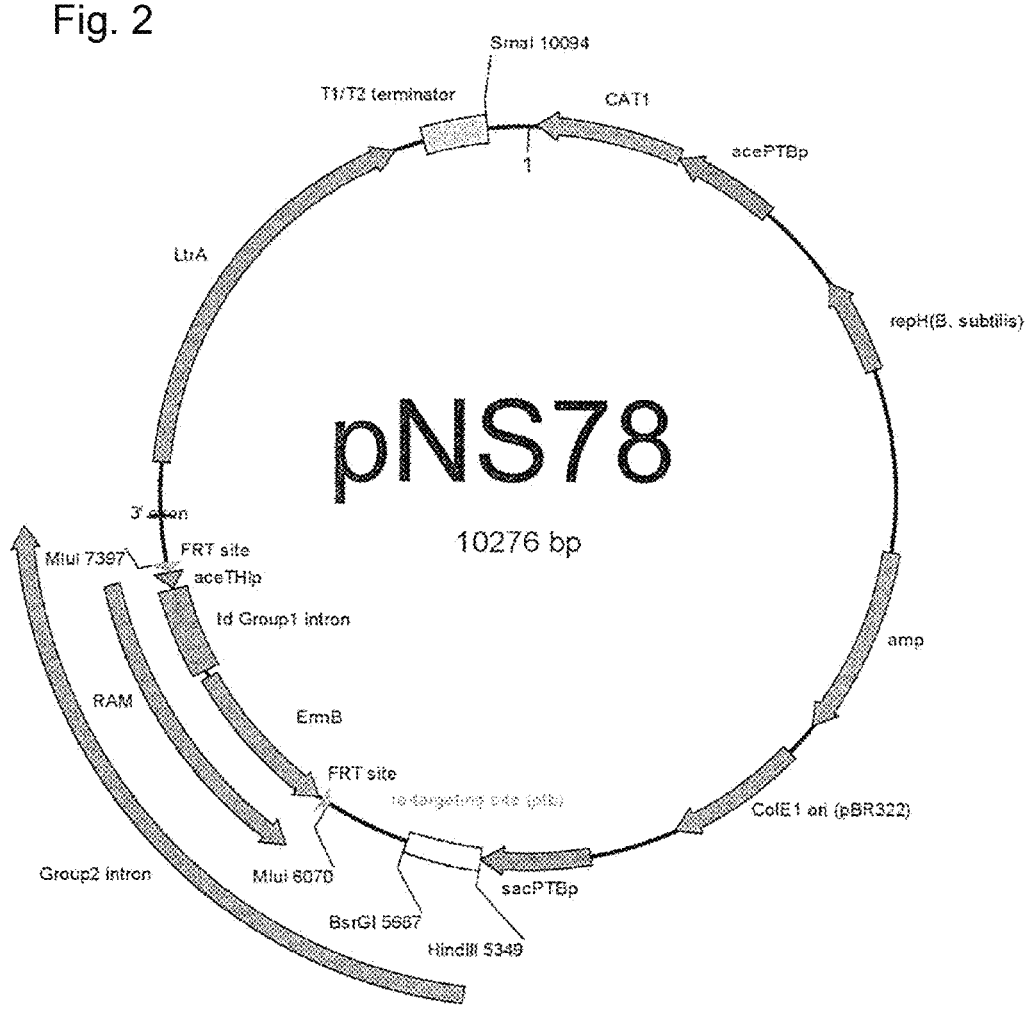
FIG. 2 shows a plasmid map of pNS78 plasmid.
Figure 3:
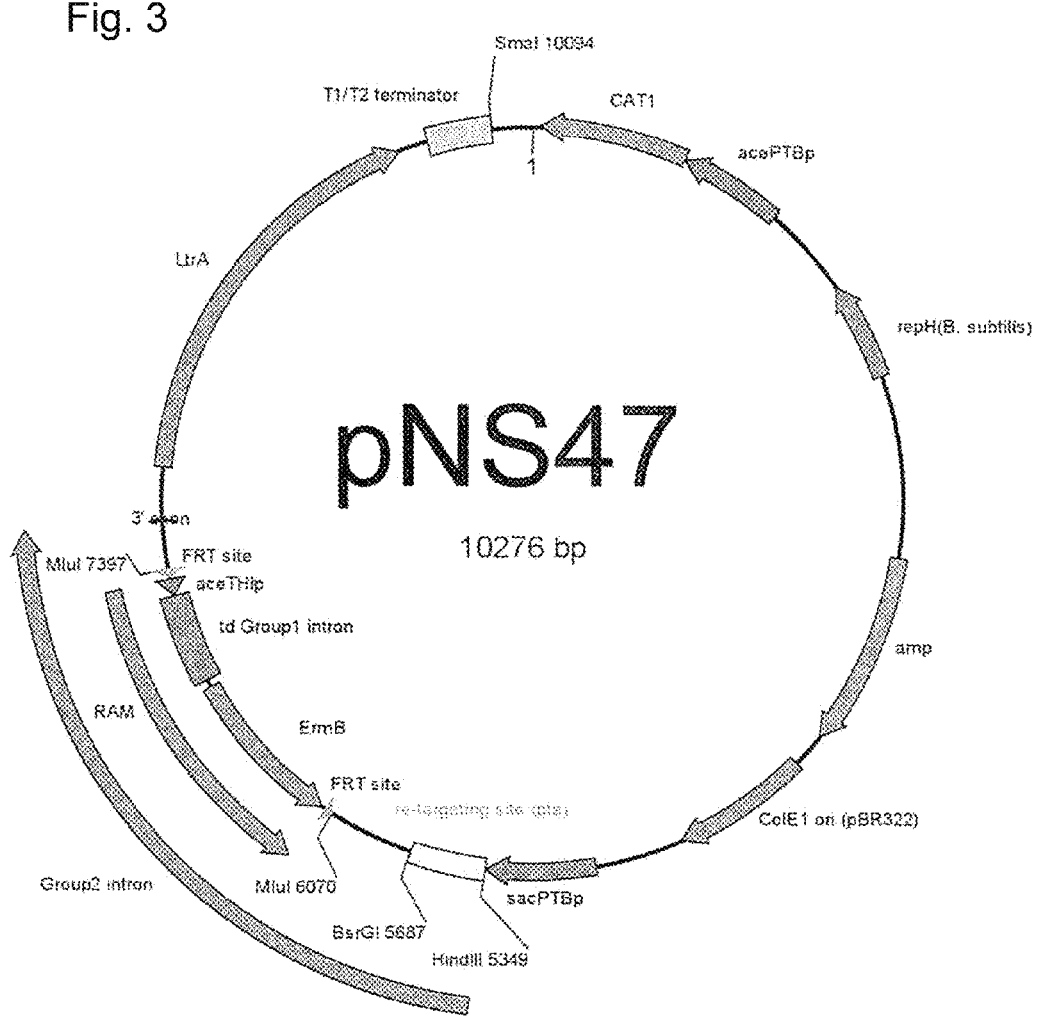
FIG. 3 shows a plasmid map of pNS47 plasmid.

Based on the data, pNS78 plasmid, pNS47 plasmid, pNS44 plasmid and pNS80 plasmid, which were disruption vectors for ptb gene, pta gene, ctfB gene and ldh1 gene, were designed. DNA synthesis was used for the construction. The nucleotide sequences of these plasmids are shown as SEQ ID NOs: 4, 5, 6 and 9, respectively and plasmid maps are shown in FIGS. 2, 3, 4 and 5. Furthermore, pKNT19-FLP plasmid containing FLP recombinase was designed and constructed similarly by DNA synthesis. The nucleotide sequence thereof is shown as SEQ ID NO: 7 and the plasmid map thereof is shown in FIG. 6.

*C. saccharoperbutylacetonicum* ATCC27021 strain was transformed with pNS78 prepared. Specifically, as preculture, a glycerol stock (0.5 ml) of *C. saccharoperbutylacetonicum* was inoculated in TYA medium (5 ml) and cultured at 30° C. for 24 hours. This preculture solution was inoculated in TYA medium (10 ml) such that OD=0.1 and incubated in a 15 mL-volume falcon tube at 37° C. When OD reached 0.6, a fermentation liquor was centrifuged and the supernatant was removed. 65 mM MOPS buffer (pH 6.5)(10 ml) cooled on ice was added thereto, resuspended by pipetting, and centrifuged. Washing with MOPS buffer was repeated twice. The MOPS buffer was centrifugally removed and the bacterial pellets were resuspended with 0.3 M sucrose (100 μL) cooled on ice to obtain competent cells. The competent cells (50 μL) was transferred to an Eppendorf tube and mixed with a plasmid (1 μg). The mixture was placed in an ice-cooled electroporation cell and voltage was applied at 2.5 kV/cm, 25 μF, 350Ω in exponential decay mode. The electroporation apparatus used was Gene pulser xcell (Bio-rad). Thereafter, the whole amount was inoculated in TYA medium (5 ml), cultured at 30° C. for about 2 hours for rescue. Thereafter, the rescue culture solution was applied onto MASS solid medium containing chloramphenicol (10 ppm), and cultured at 30° C. for several days. Screening was performed from colonies to obtain a strain in which the plasmid was introduced and resistance against chloramphenicol was acquired. The strain harboring pNS78 was further subcultured for a plurality of times and inoculated in MASS solid medium containing erythromycin (200 ppm) to obtain *C. saccharoperbutylacetonicum* Δptb strain, in which the group II intron functions, DNA sequence was inserted in the target gene, a butyric acid producing enzyme gene ptb was disrupted, and erythromycin resistance was acquired.

Since the strain has erythromycin resistance as it is and therefore disruption of a plurality of genes cannot be conducted, the erythromycin resistance gene was removed by FLP recombinase contained in pKNT19-FLP plasmid. First, *C. saccharoperbutylacetonicum* Δptb was repeatedly subcultured to obtain a strain missing pNS78 spontaneously. To the strain, pKNT19-FLP plasmid was introduced in the same electroporation method as above and screening was made based on chloramphenicol resistance. The strain having pKNT19-FLP plasmid introduced therein was repeatedly subcultured. An erythromycin sensitive strain, which was obtained by removing an erythromycin resistance gene by FLP action, was screened by a replica plate method. The erythromycin sensitive strain was subcultured to obtain *C. saccharoperbutylacetonicum* Δptb with losing pKNT19-FLP plasmid itself (non erythromycin resistant). To *C. saccharoperbutylacetonicum* Δptb having no erythromycin resistance, pNS47 and pNS44 were introduced by repeating the aforementioned method. As a result, *C. saccharoperbutylacetonicum* ΔptaΔptb strain and *C. saccharoperbutylacetonicum* ΔctfBΔptaΔptb strain in which pta gene and ctfB gene were also disrupted were successfully obtained. Further to *C. saccharoperbutylacetonicum* Δptb, pNS47 and pNS80 were introduced by repeating the aforementioned method. As a result, *C. saccharoperbutylacetonicum* ΔptaΔptbΔldh1 strain in which pta gene and ldh1 gene were also disrupted were successfully obtained. The compositions of the medium and buffer used above are shown below.

TABLE 1

Composition of TYA medium

| Component | Content (g/L) |
| --- | --- |
| D-glucose | 40 |
| Tryptone (Difco) | 6 |
| Yeast extract (Difco) | 2 |
| Ammonium acetate | 3 |
| Magnesium sulfate monohydrate | 0.3 |
| Potassium dihydrogen phosphate | 0.5 |
| Ferric sulfate (II) | 0.01 |

TABLE 2

Composition of MASS medium

| Component | Content (g/L) |
| --- | --- |
| D-glucose | 10 |
| Soluble starch | 10 |
| Potassium dihydrogen phosphate | 0.5 |
| Ammonium sulfate | 1 |
| Magnesium sulfate heptahydrate | 0.1 |
| Ferric sulfate (II) heptahydrate | 0.01 |
| Biotin | 0.00002 |

TABLE 3

Composition of MOPS buffer

| Component | Content (g/L) |
| --- | --- |
| MOPS | 209 |
| Sodium hydroxide | (added until pH reaches 6.5) |

Example 2

Butanol Fermentation by Δptb

A transformed microorganism *C. saccharoperbutylacetonicum* (Δptb strain) prepared in Example 1 was cultured and the performance of the microorganism was evaluated. 500 μL of glycerol stock of the transformed microorganism was inoculated in TYA medium and cultured in a test tube at 30° C. for 24 hours. 50 μL of the obtained preculture solution was inoculated in fresh TYS medium (5 ml) and cultured in a test tube at 30° C. for about 24 hours in open conditions.

After completion of culture, the culture solution was taken and subjected to liquid chromatography to perform quantitative analysis of butanol, other alcohols, ketones and organic acids. Aminex HPX-87H Column (Bio-Rad) was used as the column. The results are shown in Table 4. In the table, "B/(A+E+AA+BA)" represents a numerical value obtained by dividing butanol (mM) by the total of acetone (mM), ethanol (mM), acetic acid (mM) and butyric acid (mM), and is referred to as by-product parameter 1. In the table, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

TABLE 4

| | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
| --- | --- | --- | --- | --- | --- | --- | --- | --- | --- |
| TYS medium, open system, Δptb strain | 45 | 137 | 22 | 9 | 0 | 5 | 0.27 | 1.81 | 1.69 |
| TYS medium, open system, Wild strain | 69 | 113 | 17 | 10 | 0 | 10 | 0.21 | 1.18 | 1.07 |

Compared to the results of the wild strain, by-product parameter and the yield from glucose were improved in Δptb strain. Furthermore, even if $CaCO_3$ was not added, culture was successfully carried out, and the growth rate was as fast as that of the wild strain such that glucose was completely consumed at the time point of about 24 hours. Moreover, unlike the case of a precedent literature where the butyric acid production pathway for *C. acetobutyricum* was disrupted, no metabolic change such as abnormal elevation of acetic acid was observed.

Example 3

Butanol Fermentation Using ΔptaΔptb Strain

A transformed microorganism *C. saccharoperbutylacetonicum* (ΔptaΔptb strain) prepared in Example 1 was cultured and the performance of the microorganism was evaluated. 500 μL of glycerol stock of the transformed microorganism was inoculated in TYA medium (5 ml) and cultured in a test tube at 30° C. for 24 hours. 50 μL of the obtained preculture solution was inoculated in fresh TYA, TYS or TYS-$CaCO_3$ medium (5 ml) and cultured in a test tube at 30° C. The composition of TYS medium is shown below. TYS-$CaCO_3$ medium refers to a medium prepared by adding $CaCO_3$ (5 g/l) to TYS medium.

TABLE 5

| Composition of TYS medium | |
| --- | --- |
| Component | Content (g/L) |
| D-glucose | 40 |
| Tryptone (Difco) | 6 |
| Yeast extract (Difco) | 2 |
| Ammonium sulfate | 2.58 |
| Magnesium sulfate monohydrate | 0.3 |
| Potassium dihydrogen phosphate | 0.5 |
| Ferric sulfate (II) | 0.01 |

Culture was performed for about 96 hours in open conditions or closed condition. In TYS-$CaCO_3$ medium, the pH value is maintained at 5 or more so as not to be lowered by the action of $CaCO_3$. The wild strain was cultured in the same manner.

After completion of culture, the culture solution was taken and subjected to liquid chromatography to perform quantitative analysis of butanol, other alcohols, ketone and organic acids. Aminex HPX-87H Column (Bio-Rad) was used as the column. The results are shown in Tables 6 and 7. In the table, "B/(A+E+AA+BA)" represents a numerical value obtained by dividing butanol (mM) by the total of acetone (mM), ethanol (mM), acetic acid (mM) and butyric acid (mM), and is referred to as by-product parameter 1. In the table, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

TABLE 6

| Δpta Δptb strain | | | | | | | | | |
| --- | --- | --- | --- | --- | --- | --- | --- | --- | --- |
| | Acetone (mM) | Butanol (mM) | Ethanol (mM) | Acetic acid (mM) | Butyric acid (mM) | Lactic acid (mM) | Butanol/Glucose (g/g) | B/(A + E + AA + BA) (mM/mM) | B/(A + E + AA + BA + LA) (mM/mM) | Lowest pH during culture (—) |
| TYS medium, open system | 0 | 0 | 0 | 0 | 0 | 6 | 0.21 | — | — | 4.5 |
| TYS-$CaCO_3$ medium, open system | 6 | 175 | 25 | 0 | 0 | 5 | 0.29 | 5.65 | 4.86 | 5.2 |
| TYS-$CaCO_3$ medium, closed system | 3 | 184 | 10 | 0 | 0 | 6 | 0.31 | 14.15 | 9.68 | 5.7 |

TABLE 7

| Wild strain | | | | | | | | | |
| --- | --- | --- | --- | --- | --- | --- | --- | --- |
| | Acetone (mM) | Butanol (mM) | Ethanol (mM) | Acetic acid (mM) | Butyric acid (mM) | Lactic acid (mM) | Butanol/Glucose (g/g) | B/(A + E + AA + BA) (mM/mM) | B/(A + E + AA + BA + LA) (mM/mM) |
| TYS medium, open system | 69 | 113 | 17 | 10 | 0 | 5 | 0.21 | 1.18 | 1.12 |
| TYS-$CaCO_3$ medium, open system | 68 | 118 | 52 | 12 | 4 | 3 | 0.21 | 0.87 | 0.85 |
| TYS-$CaCO_3$ medium, closed system | 39 | 156 | 32 | 3 | 1 | 13 | 0.28 | 2.08 | 1.77 |

The results of Table 6 show that, when pH was not controlled with CaCO$_3$, ΔptaΔptb strain hardly grew. Since pH decreased to about 4.5, it was found that maintaining of pH to a certain level or more is necessary for growth.

Incidentally, ΔptaΔptb strain cultured in TYA medium grew well since pH was maintained at 5 or more and no pH control with CaCO$_3$ was required.

When culture was performed in TYS-CaCO$_3$ medium, the highest butanol concentration in the wild strain was 156 mM or less, whereas, in ΔptaΔptb strain, the concentration of butanol accumulated in the open system was 175 mM and the concentration of butanol accumulated in the closed system was 184 mM. In addition, no production of butyric acid and acetic acid was confirmed in ΔptaΔptb strain. Further, in the closed system, acetone concentration and ethanol concentration were suppressed as low as 3 mM and 10 mM, respectively. As a result, the by-product parameter increased up to 13.92. Although the by-product parameter increased up to 2.08 in the wild strain by performing culture in a closed-system, the parameter was still low compared to that of ΔptaΔptb strain.

Culture was performed for 96 hours in open conditions or closed condition. In closed conditions, the hydrogen partial pressure was controlled by changing the ratio of the gas-phase portion to the culture solution portion in the test tube.

After completion of culture, the culture solution was taken and subjected to liquid chromatography to perform quantitative analysis of butanol, other alcohols, ketones and organic acids. Aminex HPX-87H Column (Bio-Rad) was used as the column. The results are shown in Table 8. In the table, "B/(A+E+AA+BA)" represents a numerical value obtained by dividing butanol (mM) by the total of acetone (mM), ethanol (mM), acetic acid (mM) and butyric acid (mM), and is referred to by-product parameter 1. In the table, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

TABLE 8

|  | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Open system | 6 | 175 | 25 | 0 | 0 | 5 | 0.29 | 5.65 | 4.86 |
| Closed system Hydrogen partial pressure 0.06 atm | 4 | 175 | 13 | 0 | 0 | 10 | 0.29 | 10.29 | 6.48 |
| Closed system Hydrogen partial pressure 0.08 atm | 4 | 182 | 10 | 0 | 0 | 9 | 0.3 | 13.00 | 7.91 |
| Closed system Hydrogen partial pressure 0.10 atm | 5 | 186 | 10 | 0 | 0 | 7 | 0.31 | 12.40 | 8.45 |
| Closed system Hydrogen partial pressure 0.15 atm | 3 | 184 | 10 | 0 | 0 | 6 | 0.31 | 14.15 | 9.68 |
| Closed system Hydrogen partial pressure 0.20 atm | 4 | 184 | 11 | 0 | 0 | 5 | 0.31 | 12.27 | 9.20 |
| Closed system Hydrogen partial pressure 0.25 atm | 5 | 177 | 10 | 0 | 0 | 5 | 0.31 | 11.80 | 8.85 |

When pH was controlled with CaCO$_3$, the yield of butanol relative to by-products was higher in ΔptaΔptb strain than that in the wild strain in both of the open system and the closed system.

Example 4

Butanol Fermentation at Various Hydrogen Partial Pressures

A transformed microorganism *C. saccharoperbutylacetonicum* (ΔptaΔptb strain) prepared in Example 1 was cultured at various hydrogen partial pressures. 500 μL of glycerol stock of the transformed microorganism was inoculated in TYS-CaCO$_3$ medium and cultured in a test tube at 30° C. for 24 hours. 50 μL of the obtained preculture solution was inoculated in fresh TYS-CaCO$_3$ medium (5 ml) and cultured in a test tube at 30° C. The pH of the medium was controlled so as not to be lower than 5.0 by adding CaCO$_3$ (5 g/L)

As seen from the results of Table 8, in the case where pH was controlled with CaCO$_3$, the ethanol accumulation amount in the open system was larger than that in the closed system and the accumulation amount was about 25 mM. As the result, the by-product parameter was higher in the closed system. It demonstrates that higher hydrogen partial pressure is advantageous for performing culture with a small amount of by-products in a condition the hydrogen partial pressure is 0.25 atm or less.

Example 5

Butanol Fermentation by ΔctfBΔptaΔptb

A transformed microorganism *C. saccharoperbutylacetonicum* (ΔctfBΔtaΔptb strain) prepared in Example 1 was cultured and the performance of the microorganism was evaluated. 500 μL of glycerol stock of the transformed microorganism was inoculated in TYS-CaCO$_3$ medium and cultured in a test tube at 30° C. for 24 hours. 50 μL of the obtained preculture solution was inoculated in fresh TYS-CaCO₃ medium (5 ml) and cultured in a test tube at 30° C.

Culture was performed for 96 hours in open conditions or closed condition. In pH control conditions, the pH of the medium was controlled so as not to be lower than 5 by adding CaCO₃ (5 g/L).

After completion of culture, the culture solution was taken and subjected to liquid chromatography to perform quantitative analysis of butanol, other alcohols, ketone and organic acids. Aminex HPX-87H Column (Bio-Rad) was used as the column. The results are shown in Table 9. In the table, "B/(A+E+AA+BA)" represents a numerical value obtained by dividing butanol (mM) by the total of acetone (mM), ethanol (mM), acetic acid (mM) and butyric acid (mM), and is referred to as by-product parameter 1. In the table, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

Example 6

Butanol Fermentation by ΔptaΔptbΔldh1

A transformed microorganism *C. saccharoperbutylacetonicum* (ΔptaΔptbΔldh1 strain) prepared in Example 1 and the wild strain were cultured and the performance of the microorganisms was evaluated. 500 µL of glycerol stock of the transformed microorganism was inoculated in TYS-CaCO₃ medium and cultured in a test tube at 30° C. for 24 hours. 50 of the obtained preculture solution was inoculated in fresh TYS-CaCO₃ medium (5 ml) and cultured in a test tube at 30° C.

Culture was performed for 96 hours in open conditions or closed condition. The pH of the medium was controlled so as not to be lower than 5 by adding CaCO₃ (5 g/L)

After completion of culture, the culture solution was taken and subjected to liquid chromatography to perform quantitative analysis of butanol, other alcohols, ketone and organic acids. Aminex HPX-87H Column (Bio-Rad) was used as the column. The results are shown in Table 10. In the table, "B/(A+E+AA+BA)" represents a numerical value

TABLE 9

| | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| TYS medium, open system | 0 | 0 | 0 | 0 | 0 | | — | — | |
| TYS-CaCO₃ medium, open system | 0 | 164 | 19 | 3 | 0 | 7 | 0.29 | 7.45 | 5.66 |
| TYS-CaCO₃ medium, closed system | 0 | 168 | 16 | 2 | 0 | 2 | 0.34 | 9.33 | 8.40 |

As is similar to the results of Example 3, in the culture where pH was not controlled with CaCO₃, a phenomenon where pH falls down and the microorganism was not grown was observed. In the case where pH was controlled, the butanol yield and by-product parameter were higher in ΔctfBΔptaΔptb strain than those of the wild strain of Example 2. In ΔctfBΔptaΔptb strain, acetone was not produced and instead acetic acid was slightly produced as compared to the case of ΔptaΔptb strain.

obtained by dividing butanol (mM) by the total of acetone (mM), ethanol (mM), acetic acid (mM) and butyric acid (mM), and is referred to as by-product parameter 1. In the table, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

TABLE 10

| | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Wild strain | | | | | | | | | |
| TYS-CaCO₃ medium, open system | 68 | 118 | 52 | 12 | 4 | 3 | 0.21 | 0.87 | 0.85 |
| TYS-CaCO₃ medium, closed system | 39 | 156 | 32 | 3 | 1 | 13 | 0.28 | 2.08 | 1.77 |
| ΔptaΔptbΔldh1 | | | | | | | | | |
| TYS-CaCO₃ medium, open system | 4 | 169 | 7 | 0 | 2 | 5 | 0.32 | 13.00 | 9.39 |

TABLE 10-continued

|  | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| TYS-CaCO$_3$ medium, closed system | 5 | 179 | 15 | 0 | 1 | 3 | 0.34 | 8.52 | 7.46 |

It was found from the results of Table 10 that the yield of butanol relative to by-products was higher in ΔptaΔptbΔldh1 strain than that of the wild strain in both of the open system and the closed system. By comparing with the results of ΔptaΔptb strain shown in Table 6, it is clear that production of lactic acid is suppressed in ΔptaΔptbΔldh1 strain, particularly in the closed system and the yield of butanol relative to by-products was further improved.

Example 7

Butanol Fermentation in Different Medium Conditions

Transformed microorganisms *C. saccharoperbutylacetonicum* strains (Δpta strain, Δptb strain, ΔptaΔptb strain, ΔptaΔptbΔldh1 strain) prepared in Example 1 were cultured and the performance of the microorganisms was evaluated. 500 μL of glycerol stock of the transformed microorganism was inoculated in TYS medium (5 ml) and cultured in a test tube at 30° C. for 24 hours. 50 μL of the obtained preculture solution was inoculated in fresh TYS-KH$_2$PO$_4$ medium (5 ml) and cultured in a test tube at 30° C. The composition of TYS-KH$_2$PO$_4$ medium are shown below.

TABLE 11

Composition of TYS-KH$_2$PO$_4$ medium

| Component | Content (g/L) |
|---|---|
| D-glucose | 40 |
| Tryptone (Difco) | 6 |
| Yeast extract (Difco) | 2 |
| Ammonium sulfate | 2.58 |
| Magnesium sulfate heptahydrate | 0.3 |
| Potassium dihydrogen phosphate (KH$_2$PO$_4$) | 0.5/1.0/2.0 |
| Ferric sulfate (II) heptahydrate | 0.01 |

Culture was performed for 96 hours in closed conditions in which two conditions of initial pH: 6.5 and 7.0 were employed. The wild strain was cultured in the same manner.

After completion of culture, the culture solution was taken and subjected to liquid chromatography to perform quantitative analysis of butanol, other alcohols, ketones and organic acids. Aminex HPX-87H Column (Bio-Rad) was used as the column. The results are shown in Tables 12 to 17. In the tables, "B/(A+E+AA+BA)" represents a numerical value obtained by dividing butanol (mM) by the total of acetone (mM), ethanol (mM), acetic acid (mM) and butyric acid (mM), and is referred to as by-product parameter 1. In the tables, "B/(A+E+AA+BA+LA)" represents a numerical value obtained by dividing butanol (mM) by the total of acetone (mM), ethanol (mM), acetic acid (mM), butyric acid (mM) and lactic acid (mM) and is referred to as by-product parameter 2. In addition, by-product parameter 1 and by-product parameter 2 are collectively referred to as "by-product parameter".

TABLE 12

KH$_2$PO$_4$(0.5 g/L), Initial pH 6.5

| Strain | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Wild strain | 13 | 33 | 5 | 1 | 0 | 0 | 0.23 | 1.74 | 1.74 |
| Δpta | 19 | 113 | 25 | 0 | 0 | 0 | 0.29 | 2.57 | 2.57 |
| Δptb | 15 | 145 | 19 | 0 | 0 | 1 | 0.31 | 4.26 | 4.14 |
| ΔptaΔptb | 5 | 111 | 0 | 0 | 0 | 0 | 0.34 | 22.20 | 22.20 |
| ΔptaΔptb Δldh1 | 4 | 109 | 7 | 0 | 0 | 0 | 0.33 | 9.91 | 9.91 |

TABLE 13

KH$_2$PO$_4$(0.5 g/L), Initial pH 7.0

| Strain | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Wild strain | 12 | 31 | 5 | 2 | 0 | 0 | 0.22 | 1.63 | 1.63 |
| Δpta | 21 | 110 | 29 | 0 | 0 | 0 | 0.28 | 2.20 | 2.20 |
| Δptb | 9 | 114 | 30 | 0 | 0 | 0 | 0.30 | 2.92 | 2.92 |
| ΔptaΔptb | 7 | 127 | 8 | 0 | 0 | 0 | 0.34 | 8.47 | 8.47 |
| ΔptaΔptbΔldh1 | 4 | 119 | 8 | 0 | 0 | 0 | 0.33 | 9.92 | 9.92 |

TABLE 14

KH$_2$PO$_4$(1.0 g/L), Initial pH 6.5

| Strain | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Wild strain | 13 | 33 | 19 | 2 | 0 | 0 | 0.23 | 0.97 | 0.97 |
| Δpta | 20 | 102 | 25 | 1 | 0 | 0 | 0.28 | 2.22 | 2.22 |
| Δptb | 11 | 106 | 20 | 1 | 0 | 0 | 0.31 | 3.31 | 3.31 |
| ΔptaΔptb | 5 | 120 | 0 | 0 | 0 | 0 | 0.35 | 24.00 | 24.00 |
| ΔptaΔptbΔldh1 | 3 | 109 | 3 | 0 | 0 | 0 | 0.34 | 18.17 | 18.17 |

TABLE 15

KH$_2$PO$_4$(1.0 g/L), Initial pH 7.0

| Strain | Acetone (mM) | Butanol (mM) | Ethanol (mM) | Acetic acid (mM) | Butyric acid (mM) | Lactic acid (mM) | Butanol/ Glucose (g/g) | B/(A + E + AA + BA) (mM/mM) | B/(A + E + AA + BA + LA) (mM/mM) |
|---|---|---|---|---|---|---|---|---|---|
| Wild strain | 21 | 51 | 8 | 1 | 0 | 0 | 23.3 | 1.70 | 1.70 |
| Δpta | 36 | 141 | 22 | 0 | 0 | 0 | 26.1 | 2.43 | 2.43 |
| Δptb | 18 | 150 | 21 | 0 | 0 | 0 | 27.1 | 3.85 | 3.85 |
| ΔptaΔptb | 4 | 117 | 0 | 0 | 0 | 0 | 33.7 | 29.25 | 29.25 |
| ΔptaΔptbΔldh1 | 4 | 129 | 7 | 0 | 0 | 0 | 32.6 | 11.73 | 11.73 |

From Tables 12 to 15, it was found that butanol yield in relation to by-products is higher in the results of Δpta strain, Δptb strain, Δptaptb strain, Δptaptbldh1 strain than that in the wild strain when pH was controlled by KH$_2$PO$_4$.

The contents of all publications, patents and Japanese Patent Applications cited in the specification are incorporated in their entirety by reference.

---

The invention claimed is:

1. A *Clostridium saccharoperbutylacetonicum* strain ATCC 27021 microorganism, wherein the phosphotransbutyrylase (ptb) gene and the phosphotransacetylase (pta) gene are disrupted in the microorganism,
optionally wherein the acetoacetate decarboxylase (adc) gene or the coA transferase (ctfAB) gene is disrupted in the microorganism,
optionally wherein the lactate dehydrogenase 1 (ldh1) gene is disrupted in the microorganism, and
wherein the microorganism has an increased butanol yield as compared to a wild-type *C. saccharoperbutylacetonicum* strain ATCC 27021 microorganism.

2. The microorganism according to claim 1, wherein the adc gene or the ctfAB gene is disrupted in the microorganism.

3. The microorganism according to claim 1, wherein the ldh1 gene is disrupted in the microorganism.

4. A method for producing butanol, comprising a step of culturing the microorganism according to claim 1 in a medium containing a carbon source under conditions for butanol fermentation to thereby produce butanol.

5. The method according to claim 4, further comprising a step of collecting the butanol from the medium.

6. The microorganism according to claim 1, wherein the ptb gene, before disruption, comprises the nucleotide sequence of SEQ ID NO: 1.

7. The microorganism according to claim 1, wherein the pta gene, before disruption, comprises the nucleotide sequence of SEQ ID NO: 2.

* * * * *

SEQUENCE LISTING

<160> NUMBER OF SEQ ID NOS: 9

<210> SEQ ID NO 1
<211> LENGTH: 918
<212> TYPE: DNA
<213> ORGANISM: Clostridium Saccharoperbutylacetonicum

<400> SEQUENCE: 1
gtgcaagaaa tgagcaaaaa ctttgacgat ttattagcaa gattaaagga agttccaaca    60

```
aagaaagtgg cagtggcagt ggcacaggac gagcctgtat tagaagctat taaagaagct    120
acagacaaaa atatagctca agctatattg gttggagata agcaaaaaat acaagaaata    180
gcaaaaaaga tagacttaga tttatcaaac tatgaaataa tggatattgc agatcctaag    240
aaagctacct tagaagcagt aaaattagtt tcaagcggtc atgcagacat gttaatgaaa    300
ggtttagttg atactgctac attttttaaga agcgtattaa ataaggaagt tggattaaga    360
acaggaaagt taatgtcaca cgttgcagtg tttgatattg aaggttggga tagactatta    420 ttttttaacag atgcagcctt taatacatat ccagaattaa aggataaagt tggaatgatt    480
aataatgcag ttgtagttgc acatgcttgt ggaatagatg ttcctaaggt agcatctata    540
tgcccagtag aagtagtgaa tacaagtatg ccttcaactg tagatgcagc attattagca    600
aaaatgagtg atagaggaca atttaaaggt tgtatagttg atggacccttt tgctttagat    660 aatgcaatat cagaagaagc agctcatcat aaaggtgtta caggaaatgt tgcaggtaaa    720
gcagatgtat tattattacc aaatatgaaa acagcaaatg ttatgtataa aacattaaca    780 tattctcta aatcaagaaa tggtggatta ttagtgggaa catcagcacc agttatctta    840
acttcaagag cagattcttt tgaaacaaaa gttaactcta ttgctttagc agcattagtt    900
gcagcaaaaa ataagtaa                                                 918

<210> SEQ ID NO 2
<211> LENGTH: 1002
<212> TYPE: DNA
<213> ORGANISM: Clostridium Saccharoperbutylacetonicum

<400> SEQUENCE: 2
atggacctta tgaaaaaaat atgggcagca gctcaatctg ataaaagaag aatcgttctt     60
ccggagggaa atgaagaaag aaatattgag gctgcaggaa aaatacaaga attaggacta    120
gcatatccaa ttttaattgg tgggaaagac gaaatagaag ctaaagcaaa ggaattggat    180
gtagacttat ctggaattga aattatagat ccagagaaat cggaaaactt aaacaagtat    240
attacagcct tttatgaatt aagaaaaagt aaaggcgtaa ctatggaaaa ggctgataaa    300
attgtaagag atcctctata tttcgctaca atgatggtta aactagatga tgcagatgga    360
atggtatctg gagcagttca tacaactgga gatttattaa gaccaggatt acaaataata    420
aagacagcac caggtgtatc tgtagtttca gtttctttta atgcaagt gccaggatct    480 acttatggag aacaaggaac tcttatattc tctgactgtg cagttaaccc aaatccaaat    540
gaagaccaat tagccgctat tgctattgca acggctgaaa cagcaaagag attatgtaac    600
atggatccta agtagcaat gctgtcattc tccacaatgg gaagtgcaga taatgaattg    660
gttgataaag ttagaaatgc aacacaaaaa gcaaagaaa tgagaccaga tttagatatt    720
gatggtgaac ttcaattaga tgcagcaatt gttaaaaaag tagctgatca aaaggcacca    780
aatagtaaag tagcaggaaa agctaatgtt ttagtattcc cagatttaca agctggaaac    840 ataggtttata aattagtcca aagatttgca aatgcagaag ctattgggcc tatttgtcaa    900
ggctttgata aaccaataaa tgatttatca agaggatgta gttcagatga tatcgtaaat    960
gttgttgcat taactgctgt acaagcgcaa acaataat ag                       1002

<210> SEQ ID NO 3
<211> LENGTH: 666
<212> TYPE: DNA
<213> ORGANISM: Clostridium Saccharoperbutylacetonicum
```

<400> SEQUENCE: 3

```
ttgattgtag ataaagtttt agccaaagag ataattgcca aaagggttgc gaaagaacta      60
aaaaaaggcc aactcgtaaa ccttggaata ggacttccaa ctttagtagc aaattatgtg     120
ccgaaagaaa tgaacattac ttttgaatca gaaaatggca tggttggtat ggctcaaatg     180
gcctcatcag gtgaaaatga tccagatata ataaatgctg gtggggaata tgtaacctta     240
ttacctcaag gtgcattttt tgatagttca atgtctttcg cactaataag aggaggacat     300
gttgatgttg ctgttcttgg tgctctagaa gttgatgaaa aaggtaattt agctaactgg     360
attgttccaa ataaaattgt cccaggtatg ggaggcgcta tggatttagc aataggtgcc     420
aaaagaataa tagtggcaat gcaacatacc ggaaaaggta aacctaaaat tgtaaaaaaa     480
tgcattctcc cacttactgc taaagctcag gtagatttaa ttgttacaga gctttgtgta     540
attgatgtaa caaatgatgg tttactttta aaagaaattc ataaagatac aactattgat     600
gaaataaaat tttaacagat gcagattta attattccag ataacttaaa aattatggat     660
atctga                                                                666
```

<210> SEQ ID NO 4
<211> LENGTH: 10276
<212> TYPE: DNA
<213> ORGANISM: Artificial
<220> FEATURE:
<223> OTHER INFORMATION: Synthetic

<400> SEQUENCE: 4

```
tcacaaaaaa taggtacacg aaaaacaagt tacgccccgc cctgccactc atcgcagtac      60
tgttgtaatt cattaagcat tctgccgaca tggaagccat cacagacggc atgatgaacc     120
tgaatcgcca gcggcatcag caccttgtcg ccttgcgtat aatatttgcc catggtgaaa     180
acggggcga agaagttgtc catattggcc acgtttaaat caaaactggt gaaactcacc     240
cagggattgg ctgagacgaa aaacatattc tcaataaacc cttagggaa ataggccagg     300
ttttcaccgt aacacgccac atcttgcgaa tatatgtgta gaaactgccg gaaatcgtcg     360
tggtattcac tccagagcga tgaaaacgtt tcagtttgct catggaaaac ggtgtaacaa     420
gggtgaacac tatcccatat caccagctca ccgtcttttca ttgccatacg gaattccgga     480
tgagcattca tcaggcgggc aagaatgtga ataaaggccg gataaaactt gtgcttattt     540
ttctttacgg tctttaaaaa ggccgtaata tccagctgaa cggtctggtt ataggtacat     600
tgagcaactg actgaaatgc ctcaaaatgt tctttacgat gccattggga tatatcaacg     660
gtggtatatc cagtgatttt tttctccatt ggtcgtacac tccctttac tatttaatta     720
tctatgttaa atgattaacg tgctcattta tattttaaca aactttttcac atgaagttaa     780
gttttttaga aaattattta tatttatat tttctcatta tactttctgc tgacttaact     840
ccatccacag ccgctgatat tatgcctcct gcaaatcctg ccccttcacc tgatggatat     900
agtcctttta gtgaaatact ttcaagcgac tcattctag ttatctttaa tggagcggat     960
gttctagtct ctattccagt cattaccgcg tcagagagca tatatcctgt tatttttta    1020
tcaaaattta caagcccctc ttttagtgca gctattacat aaggtggcaa acactctgat    1080
aagctcgcaa atttatatcc tggagtataa gatggtttta cgcttcctaa tttactgctt    1140
actgtatcct tcatatataa ccctctttat ttttcctcc ttataaaatt agtataatta    1200
tagcacgagc tctgataaat atgaacatga tgagtgatcg ttaaatttat actgcaatct    1260
gatgcgatta ttgaataaaa gatatgagag atttatctag tttcttttt tacaagaaaa    1320
```

```
aagaaagttc ttaaaggttt tatacttttg gtcgtagagc acacggttta acgacttaat    1380
tacgaagtaa ataagtctag tgtgttagac tttaatgttt ttttaaggca ttagtgcatt    1440
taagcgtcag agcatggctt tatgccgaga aaactattgg ttggaatggc gtgtgtgtta    1500
gccaaaggtt aatcgcattt catagattga cctcccaata actacgtggt gttattggga    1560
ggtcaatcta tttcatttgc ctcttgctca agttcccaa attcgagtaa gaggtatttt     1620 tgttttggt cgtcgcctct cattagtagt tcagggttta acattaatac tccagttttt     1680 cttttata a tatttccttc ttctaagatt ttaagtgttg ttattactgt ttgtagactt    1740
gttcctgtag cttttgctat ttctcttgtt gtagctatca ttgtattgtt acttaagtgg    1800
acattatcta ggatatagtt aacgatttta agtttttttc cgccaatcat atctaacata    1860
cttattaatt gcactatata tgcctttacg aagttaccag acgtttgttt acggtataac    1920
ttgtctacct ctatgacttc tccactttct tcgtctatga gcctctgaga gcctttatag    1980
actgttccat atctttcttt catctttttc tcactcctta ttttaaacta ttctaactat    2040
atcataactg ttctaaaaaa aaaagaacat tgttaaaag aaattagaac aaaatgagtg      2100
aaaaattaga acaaacaaat tccttataaa ccttatcatc tcaacctata ttaagatttt    2160
acctagttga atcttctttt ctatataaag cgtcggagca tatcaggggg ttatctaacg    2220
taaatgctac ccttcggctc gctttcgctc ggcattgacg tcagatactg caccccctga    2280
acccccatgc tccaacagca aaaggaaac ttttgctgc ttttccgacg cttattcgct       2340
tcgctcatat ttatatagaa aagaagtgaa tgcgcaaaag acataatcgc ctgatgcggt    2400
attttctcct tacgcatctg tgcggtattt cacaccgcat atggtgcact ctcagtacaa    2460
tctgctctga tgccgcatag ttaagccagc cccgacaccc gccaacaccc gctgacgcgc    2520
cctgacgggc ttgtctgctc ccggcatccg cttacagaca agctgtgacc gtctccggga    2580
gctgcatgtg tcagaggttt tcaccgtcat caccgaaacg cgcgagacga aagggcctcg    2640
tgatacgcct atttttatag gttaatgtca tgataataat ggtttcttag acgtcaggtg    2700
gcacttttcg gggaaatgtg cgcggaaccc ctatttgttt attttttctaa atacattcaa   2760 atatgtatcc gctcatgaga caataaccct gataaatgct tcaataatat tgaaaaagga    2820
agagtatgag tattcaacat ttccgtgtcg cccttattcc cttttttgcg gcattttgcc    2880
ttcctgtttt tgctcaccca gaaacgctgg tgaaagtaaa agatgctgaa gatcagttgg    2940
gtgcacgagt gggttacatc gaactggatc tcaacagcgg taagatcctt gagagttttc    3000
gccccgaaga acgttttcca atgatgagca cttttaaagt tctgctatgt ggcgcggtat    3060
tatcccgtat tgacgccggg caagagcaac tcggtcgccg catacactat tctcagaatg    3120
acttggttga gtactcacca gtcacagaaa agcatcttac ggatggcatg acagtaagag    3180
aattatgcag tgctgccata accatgagtg ataacactgc ggccaactta cttctgacaa    3240
cgatcggagg accgaaggag ctaaccgctt ttttgcacaa catgggggat catgtaactc    3300
gccttgatcg ttgggaaccg gagctgaatg aagccatacc aaacgacgag cgtgacacca    3360
cgatgcctgt agcaatggca acaacgttgc gcaaactatt aactggcgaa ctacttactc    3420
tagcttcccg gcaacaatta atagactgga tggaggcgga taaagttgca ggaccacttc    3480
tgcgctcggc ccttccggct ggctggttta ttgctgataa atctggagcc ggtgagcgtg    3540
ggtctcgcgg tatcattgca gcactggggc cagatggtaa gccctcccgt atcgtagtta    3600
tctacacgac ggggagtcag gcaactatgg atgaacgaaa tagacagatc gctgagatag    3660
```

```
gtgcctcact gattaagcat tggtaactgt cagaccaagt ttactcatat atactttaga    3720
ttgatttaaa acttcatttt taatttaaaa ggatctaggt gaagatcctt tttgataatc    3780
tcatgaccaa atcccttaa cgtgagtttt cgttccactg agcgtcagac cccgtagaaa     3840
agatcaaagg atcttcttga tccttttt ttctgcgcgt aatctgctgc ttgcaaacaa     3900
aaaaaccacc gctaccagcg gtggtttgtt tgccggatca agagctacca actctttttc    3960
cgaaggtaac tggcttcagc agagcgcaga taccaaatac tgttcttcta gtgtagccgt    4020
agttaggcca ccacttcaag aactctgtag caccgcctac atacctcgct ctgctaatcc    4080
tgttaccagt ggctgctgcc agtggcgata agtcgtgtct taccgggttg gactcaagac    4140
gatagttacc ggataaggcg cagcggtcgg gctgaacggg gggttcgtgc acacagccca    4200
gcttggagcg aacgacctac accgaactga gatacctaca gcgtgagcta tgagaaagcg    4260
ccacgcttcc cgaagggaga aaggcggaca ggtatccggt aagcggcagg gtcggaacag    4320
gagagcgcac gagggagctt ccaggggaa acgcctggta tctttatagt cctgtcgggt    4380
ttcgccacct ctgacttgag cgtcgatttt tgtgatgctc gtcagggggg cggagcctat    4440
ggaaaaacgc cagcaacgcg gcctttttac ggttcctggc cttttgctgg ccttttgctc    4500
acatgttctt tcctgcgtta tcccctgatt ctgtggataa ccgtattacc gcctttgagt    4560
gagctgatac cgctcgccgc agccgaacga ccgagcgcag cgagtcagtg agcgaggaag    4620
cggaagagcg cccaatacgc aaaccgcctc tccccgcgcg ttggccgatt cattaatgca    4680
gctggcacga caggtttccc gactggaaag cgggcagtga gcgcaacgca attaatgtga    4740
gttagctcac tcattaggca ccccaggctt tacactttat gcttccggct cgtatgttgt    4800
gtggaattgt gagcggataa caatttcaca caggaaacag ctatgaccat gattacgccg    4860
ataaaaagat aaaagggtat gcacgtgaag atgcagtatt gacaggaata gaaactagaa    4920
cctcagcacc agtaacgctt aatagggatt ctaaggttga aagcgtaaat gttagtggac    4980
tttatccaac aggagaaggc gctggctttg caggtggaat aatatcagct gcagttgatg    5040
gtataaaagt tgctgaacat ataatcgaaa atttgctttt accaaaagaa atataagata    5100
tatttatgtg agtttgaaaa ataccagaga atctggtat tttttatatc aaaaatacat    5160
taaattatta aatttgttaa atttttattt aaatttaaaa ataattttct gaaaatttag    5220
catttgtact tattttttgt tacaatagaa aaagggatta taataaccat gattgatata    5280
aatttaacaa atatattaacc ttatattaaa taaataaaaa aataattatt aagtaagagg    5340
tgcaagaaaa gcttataatt atccttacaa ttcaaaggtg tgcgcccaga tagggtgtta    5400
agtcaagtag tttaaggtac tactctgtaa gataacacag aaaacagcca acctaaccga    5460
aaagcgaaag ctgatacggg aacagagcac ggttggaaag cgatgagtta cctaaagaca    5520
atcgggtacg actgagtcgc aatgttaatc agatataagg tataagttgt gtttactgaa    5580
cgcaagtttc taatttcggt taattgtcga tagaggaaag tgtctgaaac ctctagtaca    5640
aagaaaggta agttacaacc tttgacttat ctgttatcac cacatttgta caatctgtag    5700
gagaacctat gggaacgaaa cgaaagcgat gccgagaatc tgaatttacc aagacttaac    5760
actaactggg gatacctaa acaagaatgc ctaatagaaa ggaggaaaaa ggctatagca    5820
ctagagcttg aaaatcttgc aagggtacgg agtactcgta gtagtctgag aagggtaacg    5880 cccctttacat ggcaaagggg tacagttatt gtgtactaaa attaaaaatt gattagggag    5940
gaaaacctca aaatgaaacc aacaatggca atttagaaaa gaatcagtaa aaattcacaa    6000
gaaaatatag acgaagtttt tacaagactt tatcgttatc ttttacgtcc agatatttat    6060
```

```
tacgtggcga cgcgtgaagt tcctatactt tctagagaat aggaacttcg cgactcatag    6120
aattatttcc tcccgttaaa taatagataa ctattaaaaa tagacaatac ttgctcataa    6180
gtaacggtac ttaaattgtt tactttggcg tgtttcattg cttgatgaaa ctgatttta    6240 gtaaacagtt gacgatattc tcgattgacc cattttgaaa caaagtacgt atatagcttc    6300
caatatttat ctggaacatc tgtggtatgg cgggtaagtt ttattaagac actgtttact    6360
tttggtttag gatgaaagca ttccgctggc agcttaagca attgctgaat cgagacttga    6420
gtgtgcaaga gcaaccctag tgttcggtga atatccaagg tacgcttgta gaatccttct    6480
tcaacaatca gatagatgtc agacgcatgg ctttcaaaaa ccacttttt aataatttgt    6540 gtgcttaaat ggtaaggaat actcccaaca attttatacc tctgtttgtt agggaattga    6600
aactgtagaa tatcttggtg aattaaagtg acacgagtat tcagttttaa ttttctgac    6660 gataagttga atagatgact gtctaattca atagacgtta cctgtttact tattttagcc    6720
agtttcgtcg ttaaatgccc tttacctgtt ccaatttcgt aaacggtatc ggtttctttt    6780
aaattcaatt gttttattat ttggttgagt acttttcac tcgttaaaaa gttttgagaa    6840 tatttttat ttttgttcat accagcacca gaagcaccag catctcttgg gttaattgag    6900
gcctgagtat aaggtgactt atacttgtaa tctatctaaa cggggaaccct ctctagtaga    6960 caatcccgtg ctaaattgta ggactgccct ttaataaata cttctatatt taaagaggta    7020
tttatgaaaa gcggaattta tcagattaaa aatactttct ctagagaaaa tttcgtctgg    7080
attagttact tatcgtgtaa aatctgataa atggaattgg ttctacataa atgcctaacg    7140
actatccctt tggggagtag ggtcaagtga ctcgaaacga tagacaactt gctttaacaa    7200
gttggagata tagtctgctc tgcatggtga catgcagctg gatataattc cggggtaaga    7260
ttaacgacct tatctgaaca taatgccata tgaatccctc ctaatttata cgttttctct    7320
aacaacttaa ttatacccac tattattatt tttatcaata tagaagttcc tatactttct    7380
agagaatagg aacttcacgc gttgggaaat ggcaatgata gcgaaacaac gtaaaactct    7440
tgttgtatgc tttcattgtc atcgtcacgt gattcataaa cacaagtgaa tgtcgacagt    7500 gaattttac gaacgaacaa taacagagcc gtatactccg agaggggtac gtacggttcc    7560
cgaagagggt ggtgcaaacc agtcacagta atgtgaacaa ggcggtacct ccctacttca    7620
ccatatcatt ttctgcagcc ccctagaaat aattttgttt aacttaagaa aggagatata    7680
catatatggc tagatcgtcc attccgacag catcgccagt cactatggcg tgctgctagc    7740
gctatatgcg ttgatgcaat ttctatgcac tcgtagtagt ctgagaaggg taacgccctt    7800
tacatggcaa agggtacag ttattgtgta ctaaaattaa aaattgatta gggaggaaaa    7860
cctcaaaatg aaaccaacaa tggcaatttt agaagaatc agtaaaaatt cacaagaaaa    7920
tatagacgaa gttttacaa gactttatcg ttatcttta cgtccagata tttattacgt    7980
ggcgtatcaa aatttatatt ccaataaagg agcttccaca aaaggaatat tagatgatac    8040
agcggatggc tttagtgaag aaaaaataaa aaagattatt caatctttaa aagacggaac    8100
ttactatcct caacctgtac gaagaatgta tattgcaaaa aagaattcta aaaagatgag    8160
acctttagga attccaactt tcacagataa attgatccaa gaagctgtga gaataattct    8220
tgaatctatc tatgaaccgg tattcgaaga tgtgtctcac ggttttagac ctcaacgaag    8280
ctgtcacaca gctttgaaaa caatcaaaag agagtttggc ggcgcaagat ggtttgtgga    8340
gggagatata aaaggctgct tcgataatat agaccacgtt acactcattg gactcatcaa    8400
```

```
tcttaaaatc aaagatatga aaatgagcca attgatttat aaatttctaa aagcaggtta      8460
tctggaaaac tggcagtatc acaaaactta cagcggaaca cctcaaggtg gaattctatc     8520
tcctcttttg gccaacatct atcttcatga attggataag tttgttttac aactcaaaat     8580
gaagtttgac cgagaaagtc cagaaagaat aacacctgaa tatcgggagc tccacaatga     8640 gataaaaga  atttctcacc gtctcaagaa gttggagggt gaagaaaaag ctaaagttct     8700
tttagaatat caagaaaaac gtaaaagatt acccacactc ccctgtacct cacagacaaa     8760
taaagtattg aaatacgtcc ggtatgcgga cgacttcatt atctctgtta aaggaagcaa     8820
agaggactgt caatggataa aagaacaatt aaaacttttt attcataaca agctaaaaat     8880
ggaattgagt gaagaaaaaa cactcatcac acatagcagt caacccgctc gttttctggg     8940
atatgatata cgagtaagga gatctggaac gataaaacga tctggtaaag tcaaaaagag     9000
aacactcaat gggagtgtag aactccttat tcctcttcaa gacaaaattc gtcaatttat     9060
ttttgacaag aaaatagcta tccaaaagaa agatagctca tggtttccag ttcacaggaa     9120
atatcttatt cgttcaacag acttagaaat catcacaatt tataattctg aactccgcgg     9180
gatttgtaat tactacggtc tagcaagtaa ttttaaccag ctcaattatt ttgcttatct     9240
tatgaaatac agctgtctaa aaacgatagc ctccaaacat aagggaacac tttcaaaaac     9300
catttccatg tttaaagatg gaagtggttc gtgggggatc ccgtatgaga taaagcaagg     9360
taagcagcgc cgttattttg caaattttag tgaatgtaaa tccccttatc aatttacgga     9420
tgagataagt caagctcctg tattgtatgg ctatgcccgg aatactcttg aaaacaggtt     9480
aaaagctaaa tgttgtgaat tatgtgggac gtctgatgaa atacttcct  atgaaattca     9540 ccatgtcaat aaggtcaaaa atcttaaagg caaagaaaaa tgggaaatgg caatgatagc     9600
gaaacaacgt aaaaactctt  ttgtatgctt tcattgtcat cgtcacgtga ttcataaaca      9660
caagtgaatg tcgagcaccc gttctcggag cactgtccga ccgctttggc cgccgcccag      9720
tcctgctcgc ttcgctactt ggagccacta tcgactacgc gatcatggcg accacacccg      9780
tcctgtggat cgccaagctc gccgatggta gtgtggggtc tccccatgcg agagtaggga      9840
actgccagga atcaaataaa acgaaaggct cagtcgaaag actgggcctt tcgttttatc      9900
tgttgtttgt cggtgaacgc tctcctgagt aggacaaatc cgccgggagc ggatttgaac      9960
gttgcgaagc aacggcccgg agggtggcgg gcaggacgcc cgccataaac tgccaggcat    10020
caaattaagc agaaggccat cctgacggat ggccttttg  cgtttctaca aactcttcct    10080
gtcgtcatat ctacccgggt accgagctcg aattcactgg ccgtcgtttt acaacgtcgt    10140
gactgggaaa accctggcgt tacccaactt aatcgccttg cagcacatcc ccctttcgcc    10200
agctggcgta atagcgaaga ggcccgcacc gatcgccctt cccaacagtt gcgcagcctg    10260
aatggcgaat ggcgat                                                    10276
```

<210> SEQ ID NO 5
<211> LENGTH: 10276
<212> TYPE: DNA
<213> ORGANISM: Artificial
<220> FEATURE:
<223> OTHER INFORMATION: Synthetic

<400> SEQUENCE: 5

```
tcacaaaaaa taggtacacg aaaaacaagt tacgccccgc cctgccactc atcgcagtac       60
tgttgtaatt cattaagcat tctgccgaca tggaagccat cacagacggc atgatgaacc     120
tgaatcgcca gcggcatcag caccttgtcg ccttgcgtat aatatttgcc catggtgaaa     180
```

```
acgggggcga agaagttgtc catattggcc acgtttaaat caaaactggt gaaactcacc      240
cagggattgg ctgagacgaa aaacatattc tcaataaacc ctttagggaa ataggccagg      300
ttttcaccgt aacacgccac atcttgcgaa tatatgtgta gaaactgccg gaaatcgtcg      360
tggtattcac tccagagcga tgaaaacgtt tcagtttgct catggaaaac ggtgtaacaa      420
gggtgaacac tatcccatat caccagctca ccgtctttca ttgccatacg gaattccgga      480
tgagcattca tcaggcgggc aagaatgtga ataaaggccg gataaaactt gtgcttattt      540
ttctttacgg tctttaaaaa ggccgtaata tccagctgaa cggtctggtt ataggtacat      600
tgagcaactg actgaaatgc ctcaaaatgt tctttacgat gccattggga tatatcaacg      660
gtggtatatc cagtgatttt tttctccatt ggtcgtacac tcccttttac tatttaatta      720
tctatgttaa atgattaacg tgctcattta tattttaaca aacttttcac atgaagttaa      780
gttttttaga aaattattta tattttatat tttctcatta tactttctgc tgacttaact      840
ccatccacag ccgctgatat tatgcctcct gcaaatcctg ccccttcacc tgatggatat      900 agtccttta gtgaaatact ttcaagcgac tcatttctag ttatctttaa tggagcggat      960
gttctagtct ctattccagt cattaccgcg tcagagagca tatatcctgt tattttttta     1020
tcaaaattta caagcccctc ttttagtgca gctattacat aaggtggcaa acactctgat     1080
aagctcgcaa atttatatcc tggagtataa gatggtttta cgcttcctaa tttactgctt     1140
actgtatcct tcatatataa ccctctttat ttttcctcc ttataaaatt agtataatta     1200
tagcacgagc tctgataaat atgaacatga tgagtgatcg ttaaatttat actgcaatct     1260
gatgcgatta ttgaataaaa gatatgagag atttatctag tttctttttt tacaagaaaa     1320
aagaaagttc ttaaaggttt tatacttttg gtcgtagagc acacggttta acgacttaat     1380
tacgaagtaa ataagtctag tgtgttagac tttaatgttt tttaaggca ttagtgcatt     1440 taagcgtcag agcatggctt tatgccgaga aaactattgg ttggaatggc gtgtgtgtta     1500
gccaaaggtt aatcgcattt catagattga cctcccaata actacgtggt gttattggga     1560
ggtcaatcta tttcatttgc ctcttgctca aagttcccaa attcgagtaa gaggtatttt     1620
tgtttttggt cgtcgcctct cattagtagt tcagggttta acattaatac tccagttttt     1680 cttttataa tatttccttc ttctaagatt ttaagtgttg ttattactgt ttgtagactt     1740
gttcctgtag cttttgctat ttctcttgtt gtagctatca ttgtattgtt acttaagtgg     1800
acattatcta ggatatagtt aacgatttta agtttttttc cgccaatcat atctaacata     1860
cttattaatt gcactatata tgcctttacg aagttaccag acgtttgttt acggtataac     1920
ttgtctacct ctatgacttc tccactttct tcgtctatga gcctctgaga gcctttatag     1980
actgttccat atctttcttt catcttttc tcactcctta ttttaaacta ttctaactat     2040
atcataactg ttctaaaaaa aaagaacat ttgttaaaag aaattagaac aaaatgagtg     2100
aaaaattaga acaaacaaat tccttataaa ccttatcatc tcaacctata ttaagatttt     2160
acctagttga atcttctttt ctatataaag cgtcggagca tatcaggggg ttatctaacg     2220
taaatgctac ccttcggctc gctttcgctc ggcattgacg tcagatactg cacccccctga     2280 accccccatgc tccaacagca aaaggaaac ttttgctgc ttttccgacg cttattcgct     2340
tcgctcatat ttatatagaa aagaagtgaa tgcgcaaaag acataatcgc ctgatgcggt     2400
attttctcct tacgcatctg tgcggtattt cacaccgcat atggtgcact ctcagtacaa     2460
tctgctctga tgccgcatag ttaagccagc cccgacaccc gccaacaccc gctgacgcgc     2520
```

-continued

```
cctgacgggc ttgtctgctc ccggcatccg cttacagaca agctgtgacc gtctccggga    2580
gctgcatgtg tcagaggttt tcaccgtcat caccgaaacg cgcgagacga aagggcctcg    2640
tgatacgcct attttatag gttaatgtca tgataataat ggtttcttag acgtcaggtg     2700
gcacttttcg gggaaatgtg cgcggaaccc ctatttgttt attttctaa atacattcaa     2760 atatgtatcc gctcatgaga caataaccct gataaatgct tcaataatat tgaaaaagga    2820
agagtatgag tattcaacat ttccgtgtcg cccttattcc cttttttgcg gcattttgcc    2880
ttcctgtttt tgctcaccca gaaacgctgg tgaaagtaaa agatgctgaa gatcagttgg    2940
gtgcacgagt gggttacatc gaactggatc tcaacagcgg taagatcctt gagagttttc    3000
gccccgaaga acgttttcca atgatgagca cttttaaagt tctgctatgt ggcgcggtat    3060
tatcccgtat tgacgccggg caagagcaac tcggtcgccg catacactat tctcagaatg    3120
acttggttga gtactcacca gtcacagaaa agcatcttac ggatggcatg acagtaagag    3180
aattatgcag tgctgccata accatgagtg ataaacactgc ggccaactta cttctgacaa   3240
cgatcggagg accgaaggag ctaaccgctt ttttgcacaa catgggggat catgtaactc    3300
gccttgatcg ttgggaaccg gagctgaatg aagccatacc aaacgacgag cgtgacacca    3360
cgatgcctgt agcaatggca acaacgttgc gcaaactatt aactggcgaa ctacttactc    3420
tagcttcccg gcaacaatta atagactgga tggaggcgga taaagttgca ggaccacttc    3480
tgcgctcggc ccttccggct ggctggttta ttgctgataa atctggagcc ggtgagcgtg    3540
ggtctcgcgg tatcattgca gcactggggc cagatggtaa gccctcccgt atcgtagtta    3600
tctacacgac ggggagtcag gcaactatgg atgaacgaaa tagacagatc gctgagatag    3660
gtgcctcact gattaagcat tggtaactgt cagaccaagt ttactcatat atactttaga    3720
ttgatttaaa acttcatttt taatttaaaa ggatctaggt gaagatcctt tttgataatc    3780
tcatgaccaa aatcccttaa cgtgagtttt cgttccactg agcgtcagac cccgtagaaa    3840
agatcaaagg atcttcttga gatcctttt ttctgcgcgt aatctgctgc ttgcaaacaa    3900
aaaaaccacc gctaccagcg gtggtttgtt tgccggatca agagctacca actcttttc    3960 cgaaggtaac tggcttcagc agagcgcaga taccaaatac tgttcttcta gtgtagccgt    4020
agttaggcca ccacttcaag aactctgtag caccgcctac atacctcgct ctgctaatcc    4080
tgttaccagt ggctgctgcc agtggcgata agtcgtgtct taccgggttg gactcaagac    4140
gatagttacc ggataaggcg cagcggtcgg gctgaacggg gggttcgtgc acacagccca    4200
gcttggagcg aacgacctac accgaactga gatacctaca gcgtgagcta tgagaaagcg    4260
ccacgcttcc cgaagggaga aaggcggaca ggtatccggt aagcggcagg gtcggaacag    4320
gagagcgcac gagggagctt ccaggggga acgcctggta tctttatagt cctgtcgggt    4380
ttcgccacct ctgacttgag cgtcgatttt tgtgatgctc gtcagggggg cggagcctat    4440
ggaaaaacgc cagcaacgcg gcctttttac ggttcctggc cttttgctgg ccttttgctc    4500
acatgttctt tcctgcgtta tcccctgatt ctgtggataa ccgtattacc gcctttgagt    4560
gagctgatac cgctcgccgc agccgaacga ccgagcgcag cgagtcagtg agcgaggaag    4620
cggaagagcg cccaatacgc aaaccgcctc tccccgcgcg ttggccgatt cattaatgca    4680
gctggcacga caggtttccc gactggaaag cgggcagtga gcgcaacgca attaatgtga    4740
gttagctcac tcattaggca ccccaggctt tacactttat gcttccggct cgtatgttgt    4800
gtggaattgt gagcggataa caatttcaca caggaaacag ctatgaccat gattacgccg    4860
ataaaaagat aaaagggtat gcacgtgaag atgcagtatt gacaggaata gaaactagaa    4920
```

```
cctcagcacc agtaacgctt aatagggatt ctaaggttga aagcgtaaat gttagtggac    4980
tttatccaac aggagaaggc gctggctttg caggtggaat aatatcagct gcagttgatg    5040
gtataaaagt tgctgaacat ataatcgaaa aatttgcttt accaaaagaa atataagata    5100
tatttatgtg agtttgaaaa ataccagaga atctggtat tttttatatc aaaaatacat    5160
taaattatta aattttgttaa attttttattt aaatttaaaa ataattttct gaaaatttag    5220
catttgtact tatttttttgt tacaatagaa aaagggatta taataaccat gattgatata    5280
aatttaacaa atattaacc ttatattaaa taaataaaaa aataattatt aagtaagagg    5340
tgcaagaaaa gctataatt atccttaata atcgccaaag tgcgcccaga tagggtgtta    5400
agtcaagtag tttaaggtac tactctgtaa gataacacag aaaacagcca acctaaccga    5460
aaagcgaaag ctgatacggg aacagagcac ggttggaaag cgatgagtta cctaaagaca    5520
atcgggtacg actgagtcgc aatgttaatc agatataagg tataagttgt gtttactgaa    5580
cgcaagtttc taatttcggt tattatccga tagaggaaag tgtctgaaac ctctagtaca    5640
aagaaaggta agttactttt ggcgacttat ctgttatcac cacatttgta caatctgtag    5700
gagaacctat gggaacgaaa cgaaagcgat gccgagaatc tgaatttacc aagacttaac    5760
actaactggg gataccctaa acaagaatgc ctaatagaaa ggaggaaaaa ggctatagca    5820
ctagagcttg aaaatcttgc aagggtacgg agtactcgta gtagtctgag aagggtaacg    5880
ccctttacat ggcaaagggg tacagttatt gtgtactaaa attaaaaatt gattagggag    5940
gaaaacctca aaatgaaacc aacaatggca attttagaaa gaatcagtaa aaattcacaa    6000
gaaaatatag acgaagtttt tacaagactt tatcgttatc ttttacgtcc agatatttat    6060
tacgtggcga cgcgtgaagt tcctatactt tctagagaat aggaacttcg cgactcatag    6120
aattatttcc tcccgttaaa taatagataa ctattaaaaa tagacaatac ttgctcataa    6180
gtaacggtac ttaaattgtt tactttggcg tgtttcattg cttgatgaaa ctgatttta    6240 gtaaacagtt gacgatattc tcgattgacc cattttgaaa caaagtacgt atatagcttc    6300
caatatttat ctggaacatc tgtggtatgg cgggtaagtt ttattaagac actgtttact    6360
tttggtttag gatgaaagca ttccgctggc agcttaagca attgctgaat cgagacttga    6420
gtgtgcaaga gcaaccctag tgttcggtga atatccaagg tacgcttgta gaatccttct    6480
tcaacaatca gatagatgtc agacgcatgg cttcaaaaa ccactttttt aataatttgt    6540
gtgcttaaat ggtaaggaat actcccaaca attttatacc tctgtttgtt agggaattga    6600
aactgtagaa tatcttggtg aattaaagtg acacgagtat tcagttttaa ttttctgac    6660 gataagttga atagatgact gtctaattca atagacgtta cctgtttact tattttagcc    6720
agtttcgtcg ttaaatgccc tttacctgtt ccaatttcgt aaacggtatc ggtttctttt    6780
aaattcaatt gttttattat ttggttgagt acttttcac tcgttaaaaa gttttgagaa    6840 tatttttatat ttttgttcat accagcacca gaagcaccag catctcttgg gttaattgag    6900
gcctgagtat aaggtgactt atacttgtaa tctatctaaa cggggaacct ctctagtaga    6960
caatcccgtg ctaaattgta ggactgccct ttaataaata cttctatatt taaagaggta    7020
tttatgaaaa gcggaattta tcagattaaa aatactttct ctagagaaaa tttcgtctgg    7080
attagttact tatcgtgtaa aatctgataa atggaattgg ttctacataa atgcctaacg    7140
actatccctt tggggagtag ggtcaagtga ctcgaaacga tagacaactt gctttaacaa    7200
gttggagata tagtctgctc tgcatggtga catgcagctg gatataattc cggggtaaga    7260
```

```
ttaacgacct tatctgaaca taatgccata tgaatccctc ctaatttata cgttttctct      7320
aacaacttaa ttatacccac tattattatt tttatcaata tagaagttcc tatactttct      7380
agagaatagg aacttcacgc gttgggaaat ggcaatgata gcgaaacaac gtaaaactct      7440
tgttgtatgc tttcattgtc atcgtcacgt gattcataaa cacaagtgaa tgtcgacagt      7500
gaatttttac gaacgaacaa taacagagcc gtatactccg agagggtac gtacggttcc       7560 cgaagagggt ggtgcaaacc agtcacagta atgtgaacaa ggcggtacct ccctacttca      7620
ccatatcatt ttctgcagcc ccctagaaat aattttgttt aactttaaga aggagatata      7680
catatatggc tagatcgtcc attccgacag catcgccagt cactatggcg tgctgctagc      7740
gctatatgcg ttgatgcaat ttctatgcac tcgtagtagt ctgagaaggg taacgccctt      7800
tacatggcaa aggggtacag ttattgtgta ctaaaattaa aaattgatta gggaggaaaa      7860
cctcaaaatg aaaccaacaa tggcaatttt agaaagaatc agtaaaaatt cacaagaaaa      7920
tatagacgaa gttttacaa gactttatcg ttatctttta cgtccagata tttattacgt       7980
ggcgtatcaa aatttatatt ccaataaagg agcttccaca aaaggaatat tagatgatac      8040
agcggatggc tttagtgaag aaaaaataaa aaagattatt caatctttaa aagacggaac      8100
ttactatcct caacctgtac gaagaatgta tattgcaaaa aagaattcta aaaagatgag      8160
acctttagga attccaactt tcacagataa attgatccaa gaagctgtga gaataattct      8220
tgaatctatc tatgaaccgg tattcgaaga tgtgtctcac ggttttagac ctcaacgaag      8280
ctgtcacaca gctttgaaaa caatcaaaag agagtttggc ggcgcaagat ggtttgtgga      8340
gggagatata aaaggctgct tcgataatat agaccacgtt acactcattg gactcatcaa      8400
tcttaaaatc aaagatatga aaatgagcca attgatttat aaatttctaa agcaggtta      8460 tctgaaaaac tggcagtatc acaaaactta cagcggaaca cctcaaggtg gaattctatc      8520
tcctcttttg gccaacatct atcttcatga attggataag tttgttttac aactcaaaat      8580
gaagtttgac cgagaaagtc cagaaagaat aacacctgaa tatcgggagc tccacaatga      8640
gataaaaaga atttctcacc gtctcaagaa gttggagggt gaagaaaaag ctaaagttct      8700
tttagaatat caagaaaaac gtaaaagatt acccacactc ccctgtacct cacagacaaa      8760
taaagtattg aaatacgtcc ggtatgcgga cgacttcatt atctctgtta aaggaagcaa      8820
agaggactgt caatggataa agaacaatt aaaacttttt attcataaca agctaaaaat      8880
ggaattgagt gaagaaaaaa cactcatcac acatagcagt caacccgctc gttttctggg      8940
atatgatata cgagtaagga gatctggaac gataaaacga tctggtaaag tcaaaaagag      9000
aacactcaat gggagtgtag aactccttat tcctcttcaa gacaaaattc gtcaatttat      9060
ttttgacaag aaaatagcta tccaaaagaa agatagctca tggtttccag ttcacaggaa      9120
atatcttatt cgttcaacag acttagaaat catcacaatt tataattctg aactccgcgg      9180
gatttgtaat tactacggtc tagcaagtaa ttttaaccag ctcaattatt ttgcttatct      9240
tatggaatac agctgtctaa aaacgatagc ctccaaacat aagggaacac tttcaaaaac      9300
catttccatg tttaaagatg gaagtggttc gtgggggatc ccgtatgaga taaagcaagg      9360
taagcagcgc cgttattttg caaattttag tgaatgtaaa tccccttatc aatttacgga      9420
tgagataagt caagctcctg tattgtatgg ctatgcccgg aatactcttg aaaacaggtt      9480
aaaagctaaa tgttgtgaat tatgtgggac gtctgatgaa atacttcct atgaaattca       9540 ccatgtcaat aaggtcaaaa atcttaaagg caaagaaaaa tgggaaatgg caatgatagc      9600
gaaacaacgt aaaactcttg ttgtatgctt tcattgtcat cgtcacgtga ttcataaaca      9660
```

```
caagtgaatg tcgagcaccc gttctcggag cactgtccga ccgctttggc cgccgcccag    9720
tcctgctcgc ttcgctactt ggagccacta tcgactacgc gatcatggcg accacacccg    9780
tcctgtggat cgccaagctc gccgatggta gtgtggggtc tccccatgcg agagtaggga    9840
actgccaggc atcaaataaa acgaaaggct cagtcgaaag actgggcctt tcgttttatc    9900
tgttgtttgt cggtgaacgc tctcctgagt aggacaaatc cgccgggagc ggatttgaac    9960
gttgcgaagc aacggcccgg agggtggcgg gcaggacgcc cgccataaac tgccaggcat   10020
caaattaagc agaaggccat cctgacggat ggcctttttg cgtttctaca aactcttcct   10080
gtcgtcatat ctacccgggt accgagctcg aattcactgg ccgtcgtttt acaacgtcgt   10140
gactgggaaa accctggcgt tacccaactt aatcgccttg cagcacatcc cctttcgcc    10200 agctggcgta atagcgaaga ggcccgcacc gatcgccctt cccaacagtt gcgcagcctg   10260
aatggcgaat ggcgat                                                   10276

<210> SEQ ID NO 6
<211> LENGTH: 10276
<212> TYPE: DNA
<213> ORGANISM: Artificial
<220> FEATURE:
<223> OTHER INFORMATION: Synthetic

<400> SEQUENCE: 6
tcacaaaaaa taggtacacg aaaaacaagt tacgccccgc cctgccactc atcgcagtac      60
tgttgtaatt cattaagcat tctgccgaca tggaagccat cacagacggc atgatgaacc     120
tgaatcgcca gcggcatcag caccttgtcg ccttgcgtat aatatttgcc catggtgaaa     180 acggggggcga agaagttgtc catattggcc acgtttaaat caaaactggt gaaactcacc     240
cagggattgg ctgagacgaa aaacatattc tcaataaacc ctttagggaa ataggccagg     300
ttttcaccgt aacacgccac atcttgcgaa tatatgtgta gaaactgccg gaaatcgtcg     360
tggtattcac tccagagcga tgaaaacgtt tcagtttgct catggaaaac ggtgtaacaa     420
gggtgaacac tatcccatat caccagctca ccgtctttca ttgccatacg gaattccgga     480
tgagcattca tcaggcgggc aagaatgtga ataaaggccg gataaaactt gtgcttattt     540
ttctttacgg tctttaaaaa ggccgtaata tccagctgaa cggtctggtt ataggtacat     600
tgagcaactg actgaaatgc ctcaaaatgt tctttacgat gccattggga tatatcaacg     660
gtggtatatc cagtgatttt tttctccatt ggtcgtacac tcccttttac tatttaatta     720
tctatgttaa atgattaacg tgctcattta tattttaaca aacttttcac atgaagttaa     780
gttttttaga aaattattta tattttatat tttctcatta tactttctgc tgacttaact     840
ccatccacag ccgctgatat tatgcctcct gcaaatcctg ccccttcacc tgatggatat     900
agtcctttta gtgaaatact ttcaagcgac tcatttctag ttatctttaa tggagcggat     960
gttctagtct ctattccagt cattaccgcg tcagagagca tatatcctgt tattttttta    1020
tcaaaattta caagcccctc ttttagtgca gctattacat aaggtggcaa acactctgat    1080
aagctcgcaa atttatatcc tggagtataa gatggtttta cgcttcctaa tttactgctt    1140
actgtatcct tcatatataa ccctctttat ttttcctcc ttataaaatt agtataatta    1200
tagcacgagc tctgataaat atgaacatga tgagtgatcg ttaaatttat actgcaatct    1260
gatgcgatta ttgaataaaa gatatgagag atttatctag tttctttttt tacaagaaaa    1320
aagaaagttc ttaaaggttt tatacttttg gtcgtagagc acacggttta acgacttaat    1380
```

```
tacgaagtaa ataagtctag tgtgttagac tttaatgttt ttttaaggca ttagtgcatt      1440
taagcgtcag agcatggctt tatgccgaga aaactattgg ttggaatggc gtgtgtgtta      1500
gccaaaggtt aatcgcattt catagattga cctcccaata actacgtggt gttattggga      1560
ggtcaatcta tttcatttgc ctcttgctca aagttcccaa attcgagtaa gaggtatttt      1620 tgttttggt cgtcgcctct cattagtagt tcagggttta acattaatac tccagttttt      1680 cttttataa tatttccttc ttctaagatt ttaagtgttg ttattactgt ttgtagactt      1740
gttcctgtag cttttgctat ttctcttgtt gtagctatca ttgtattgtt acttaagtgg      1800
acattatcta ggatatagtt aacgatttta agtttttttc cgccaatcat atctaacata      1860
cttattaatt gcactatata tgcctttacg aagttaccag acgtttgttt acggtataac      1920
ttgtctacct ctatgacttc tccactttct tcgtctatga gcctctgaga gcctttatag      1980
actgttccat atctttcttt catctttttc tcactcctta ttttaaacta ttctaactat      2040
atcataactg ttctaaaaaa aaagaacat ttgttaaaag aaattagaac aaaatgagtg      2100
aaaaattaga acaaacaaat tccttataaa ccttatcatc tcaacctata ttaagatttt      2160
acctagttga atcttctttt ctatataaag cgtcggagca tatcaggggg ttatctaacg      2220
taaatgctac ccttcggctc gctttcgctc ggcattgacg tcagatactg cacccccctga     2280 accccccatgc tccaacagca aaaggaaac ttttgctgc ttttccgacg cttattcgct      2340
tcgctcatat ttatatagaa aagaagtgaa tgcgcaaaag acataatcgc ctgatgcggt      2400
attttctcct tacgcatctg tgcggtattt cacaccgcat atggtgcact ctcagtacaa      2460
tctgctctga tgccgcatag ttaagccagc cccgacaccc gccaacaccc gctgacgcgc      2520
cctgacgggc ttgtctgctc ccggcatccg cttacagaca agctgtgacc gtctccggga      2580
gctgcatgtg tcagaggttt tcaccgtcat caccgaaacg cgcgagacga agggcctcg      2640 tgatacgcct attttatag gttaatgtca tgataataat ggtttcttag acgtcaggtg      2700
gcacttttcg gggaaatgtg cgcggaaccc ctatttgttt attttctaa atacattcaa      2760 atatgtatcc gctcatgaga caataaccct gataaatgct tcaataatat tgaaaagga      2820 agagtatgag tattcaacat ttccgtgtcg cccttattcc cttttttgcg cattttgcc      2880 ttcctgtttt tgctcaccca gaaacgctgg tgaaagtaaa agatgctgaa gatcagttgg      2940
gtgcacgagt gggttacatc gaactggatc tcaacagcgg taagatcctt gagagttttc      3000
gccccgaaga acgttttcca atgatgagca cttttaaagt tctgctatgt ggcgcggtat      3060
tatcccgtat tgacgccggg caagagcaac tcggtcgccg catacactat tctcagaatg      3120
acttggttga gtactcacca gtcacagaaa agcatcttac ggatggcatg acagtaagag      3180
aattatgcag tgctgccata accatgagtg ataacactgc ggccaactta cttctgacaa      3240
cgatcggagg accgaaggag ctaaccgctt ttttgcacaa catgggggat catgtaactc      3300
gccttgatcg ttgggaaccg gagctgaatg aagccatacc aaacgacgag cgtgacacca      3360
cgatgcctgt agcaatggca acaacgttgc gcaaactatt aactggcgaa ctacttactc      3420
tagcttcccg gcaacaatta atagactgga tggaggcgga taaagttgca ggaccacttc      3480
tgcgctcggc ccttccggct ggctggttta ttgctgataa atctggagcc ggtgagcgtg      3540
ggtctcgcgg tatcattgca gcactgggc cagatggtaa gccctcccgt atcgtagtta      3600
tctacacgac ggggagtcag gcaactatgg atgaacgaaa tagacagatc gctgagatag      3660
gtgcctcact gattaagcat tggtaactgt cagaccaagt ttactcatat atactttaga      3720
ttgatttaaa acttcatttt taatttaaaa ggatctaggt gaagatcctt tttgataatc      3780
```

```
tcatgaccaa aatcccttaa cgtgagtttt cgttccactg agcgtcgac cccgtagaaa    3840 agatcaaagg atcttcttga gatccttttt ttctgcgcgt aatctgctgc ttgcaaacaa    3900
aaaaaccacc gctaccagcg gtggtttgtt tgccggatca agagctacca actctttttc    3960
cgaaggtaac tggcttcagc agagcgcaga taccaaatac tgttcttcta gtgtagccgt    4020
agttaggcca ccacttcaag aactctgtag caccgcctac atacctcgct ctgctaatcc    4080
tgttaccagt ggctgctgcc agtggcgata agtcgtgtct taccgggttg gactcaagac    4140
gatagttacc ggataaggcg cagcggtcgg gctgaacggg gggttcgtgc acacagccca    4200
gcttggagcg aacgacctac accgaactga gatacctaca gcgtgagcta tgagaaagcg    4260
ccacgcttcc cgaagggaga aaggcggaca ggtatccggt aagcggcagg gtcggaacag    4320
gagagcgcac gagggagctt ccaggggaa acgcctggta tctttatagt cctgtcgggt    4380
ttcgccacct ctgacttgag cgtcgatttt tgtgatgctc gtcagggggg cggagcctat    4440
ggaaaaacgc cagcaacgcg gccttttac ggttcctggc cttttgctgg ccttttgctc    4500
acatgttctt cctgcgtta tcccctgatt ctgtggataa ccgtattacc gcctttgagt    4560
gagctgatac cgctcgccgc agccgaacga ccgagcgcag cgagtcagtg agcgaggaag    4620
cggaagagcg cccaatacgc aaaccgcctc tccccgcgcg ttggccgatt cattaatgca    4680
gctggcacga caggtttccc gactggaaag cgggcagtga gcgcaacgca attaatgtga    4740
gttagctcac tcattaggca ccccaggctt tacactttat gcttccggct cgtatgttgt    4800
gtggaattgt gagcggataa caatttcaca caggaaacag ctatgaccat gattacgccg    4860
ataaaaagat aaaagggtat gcacgtgaag atgcagtatt gacaggaata gaaactagaa    4920
cctcagcacc agtaacgctt aatagggatt ctaaggttga aagcgtaaat gttagtggac    4980
tttatccaac aggagaaggc gctggctttg caggtggaat aatatcagct gcagttgatg    5040
gtataaaagt tgctgaacat ataatcgaaa aatttgcttt accaaaagaa atataagata    5100
tatttatgtg agtttgaaaa ataccagaga aatctggtat tttttatatc aaaaatacat    5160
taaattatta aatttgttaa attttatttt aaattttaaaa ataattttct gaaaatttag    5220
catttgtact tattttttgt tacaatagaa aaagggatta taataaccat gattgatata    5280
aatttaacaa aatattaacc ttatattaaa taaataaaaa aataattatt aagtaagagg    5340
tgcaagaaaa gcttataatt atccttagaa gccattgggg tgcgcccaga tagggtgtta    5400
agtcaagtag tttaaggtac tactctgtaa gataacacag aaaacagcca acctaaccga    5460
aaagcgaaag ctgatacggg aacagagcac ggttggaaag cgatgagtta cctaaagaca    5520
atcgggtacg actgagtcgc aatgttaatc agatataagg tataagttgt gtttactgaa    5580
cgcaagtttc taatttcgat tgcttctcga tagaggaaag tgtctgaaac ctctagtaca    5640
aagaaaggta agttaggccc aatgacttat ctgttatcac cacatttgta caatctgtag    5700
gagaacctat gggaacgaaa cgaaagcgat gccgagaatc tgaatttacc aagacttaac    5760
actaactggg gataccctaa acaagaatgc ctaatagaaa ggaggaaaaa ggctatagca    5820
ctagagcttg aaaatcttgc aagggtacgg agtactcgta gtagtctgag aagggtaacg    5880 cccctttacat ggcaaagggg tacagttatt gtgtactaaa attaaaaatt gattagggag    5940
gaaaacctca aaatgaaacc aacaatggca attttagaaa gaatcagtaa aaattcacaa    6000
gaaaatatag acgaagtttt tacaagactt tatcgttatc ttttacgtcc agatatttat    6060
tacgtggcga cgcgtgaagt tcctatactt tctagagaat aggaacttcg cgactcatag    6120
```

```
aattatttcc tcccgttaaa taatagataa ctattaaaaa tagacaatac ttgctcataa    6180
gtaacggtac ttaaattgtt tactttggcg tgtttcattg cttgatgaaa ctgatttta     6240 gtaaacagtt gacgatattc tcgattgacc cattttgaaa caaagtacgt atatagcttc    6300
caatatttat ctggaacatc tgtggtatgg cgggtaagtt ttattaagac actgtttact    6360
tttggtttag gatgaaagca ttccgctggc agcttaagca attgctgaat cgagacttga    6420
gtgtgcaaga gcaaccctag tgttcggtga atatccaagg tacgcttgta gaatccttct    6480
tcaacaatca gatagatgtc agacgcatgg ctttcaaaaa ccactttttt aataatttgt    6540
gtgcttaaat ggtaaggaat actcccaaca atttttatacc tctgtttgtt agggaattga    6600
aactgtagaa tatcttggtg aattaaagtg acacgagtat tcagttttaa tttttctgac    6660
gataagttga atagatgact gtctaattca atagacgtta cctgtttact tattttagcc    6720
agtttcgtcg ttaaatgccc tttacctgtt ccaatttcgt aaacggtatc ggtttctttt    6780
aaattcaatt gttttattat ttggttgagt acttttcac tcgttaaaaa gttttgagaa     6840
tattttatat ttttgttcat accagcacca gaagcaccag catctcttgg gttaattgag    6900
gcctgagtat aaggtgactt atacttgtaa tctatctaaa cggggaacct ctctagtaga    6960
caatcccgtg ctaaattgta ggactgccct ttaataaata cttctatatt taagaggta    7020 tttatgaaaa gcggaattta tcagattaaa aatactttct ctagagaaaa tttcgtctgg    7080
attagttact tatcgtgtaa aatctgataa atggaattgg ttctacataa atgcctaacg    7140
actatccctt tggggagtag ggtcaagtga ctcgaaacga tagacaactt gctttaacaa    7200
gttggagata tagtctgctc tgcatggtga catgcagctg gatataattc cggggtaaga    7260
ttaacgacct tatctgaaca taatgccata tgaatccctc ctaatttata cgttttctct    7320
aacaacttaa ttatacccac tattattatt tttatcaata tagaagttcc tatactttct    7380
agagaatagg aacttcacgc gttgggaaat ggcaatgata gcgaaacaac gtaaaactct    7440
tgttgtatgc tttcattgtc atcgtcacgt gattcataaa cacaagtgaa tgtcgacagt    7500 gaattttac gaacgaacaa taacagagcc gtatactccg agaggggtac gtacggttcc    7560
cgaagagggt ggtgcaaacc agtcacagta atgtgaacaa ggcggtacct ccctacttca    7620
ccatatcatt ttctgcagcc ccctagaaat aattttgttt aactttaaga aggagatata    7680
catatatggc tagatcgtcc attccgacag catcgccagt cactatggcg tgctgctagc    7740
gctatatgcg ttgatgcaat ttctatgcac tcgtagtagt ctgagaaggg taacgccctt    7800
tacatggcaa aggggtacag ttattgtgta ctaaaattaa aaattgatta gggaggaaaa    7860
cctcaaaatg aaaccaacaa tggcaatttt agaaagaatc agtaaaaatt cacaagaaaa    7920
tatagacgaa gtttttacaa gactttatcg ttatcttta cgtccagata tttattacgt     7980
ggcgtatcaa aatttatatt ccaataaagg agcttccaca aaaggaatat tagatgatac    8040
agcggatggc tttagtgaag aaaaaataaa aaagattatt caatctttaa aagacggaac    8100
ttactatcct caacctgtac gaagaatgta tattgcaaaa aagaattcta aaaagatgag    8160
acctttagga attccaactt tcacagataa attgatccaa gaagctgtga gaataattct    8220
tgaatctatc tatgaaccgg tattcgaaga tgtgtctcac ggttttagac tcaacgaag    8280 ctgtcacaca gctttgaaaa caatcaaaag agagtttggc ggcgcaagat ggtttgtgga    8340
gggagatata aaaggctgct tcgataatat agaccacgtt acactcattg gactcatcaa    8400
tcttaaaatc aaagatatga aaatgagcca attgatttat aaatttctaa aagcaggtta    8460
tctggaaaac tggcagtatc acaaaactta cagcggaaca cctcaaggtg gaattctatc    8520
```

| | | |
|---|---|---|
| tcctcttttg gccaacatct atcttcatga attggataag tttgttttac aactcaaaat | 8580 | |
| gaagtttgac cgagaaagtc cagaaagaat aacacctgaa tatcgggagc tccacaatga | 8640 | |
| gataaaaaga atttctcacc gtctcaagaa gttggagggt gaagaaaaag ctaaagttct | 8700 | |
| tttagaatat caagaaaaac gtaaaagatt acccacactc ccctgtacct cacagacaaa | 8760 | |
| taaagtattg aaatacgtcc ggtatgcgga cgacttcatt atctctgtta aaggaagcaa | 8820 | |
| agaggactgt caatggataa aagaacaatt aaaactttt attcataaca agctaaaaat | 8880 | |
| ggaattgagt gaagaaaaaa cactcatcac acatagcagt caacccgctc gttttctggg | 8940 | |
| atatgatata cgagtaagga gatctggaac gataaaacga tctggtaaag tcaaaaagag | 9000 | |
| aacactcaat gggagtgtag aactccttat tcctcttcaa gacaaaattc gtcaatttat | 9060 | |
| ttttgacaag aaaatagcta tccaaaagaa agatagctca tggtttccag ttcacaggaa | 9120 | |
| atatcttatt cgttcaacag acttagaaat catcacaatt tataattctg aactccgcgg | 9180 | |
| gatttgtaat tactacggtc tagcaagtaa ttttaaccag ctcaattatt ttgcttatct | 9240 | |
| tatggaatac agctgtctaa aaacgatagc ctccaaacat aagggaacac tttcaaaaac | 9300 | |
| catttccatg tttaaagatg gaagtggttc gtgggggatc ccgtatgaga taaagcaagg | 9360 | |
| taagcagcgc cgttattttg caaattttag tgaatgtaaa tccccttatc aatttacgga | 9420 | |
| tgagataagt caagctcctg tattgtatgg ctatgcccgg aatactcttg aaaacaggtt | 9480 | |
| aaaagctaaa tgttgtgaat tatgtgggac gtctgatgaa aatacttcct atgaaattca | 9540 | |
| ccatgtcaat aaggtcaaaa atcttaaagg caaagaaaaa tgggaaatgg caatgatagc | 9600 | |
| gaaacaacgt aaaactcttg ttgtatgctt tcattgtcat cgtcacgtga ttcataaaca | 9660 | |
| caagtgaatg tcgagcaccc gttctcggag cactgtccga ccgctttggc cgccgcccag | 9720 | |
| tcctgctcgc ttcgctactt ggagccacta tcgactacgc gatcatggcg accacacccg | 9780 | |
| tcctgtggat cgccaagctc gccgatggta gtgtggggtc tccccatgcg agagtaggga | 9840 | |
| actgccaggc atcaaataaa acgaaaggct cagtcgaaag actgggcctt tcgttttatc | 9900 | |
| tgttgtttgt cggtgaacgc tctcctgagt aggacaaatc cgccgggagc ggatttgaac | 9960 | |
| gttgcgaagc aacggcccgg agggtggcgg gcaggacgcc cgccataaac tgccaggcat | 10020 | |
| caaattaagc agaaggccat cctgacggat ggcctttttg cgtttctaca aactcttcct | 10080 | |
| gtcgtcatat ctacccgggt accgagctcg aattcactgg ccgtcgtttt acaacgtcgt | 10140 | |
| gactgggaaa accctggcgt tacccaactt aatcgccttg cagcacatcc cctttcgcc | 10200 | |
| agctggcgta atagcgaaga ggcccgcacc gatcgccctt cccaacagtt gcgcagcctg | 10260 | |
| aatggcgaat ggcgat | 10276 | |

<210> SEQ ID NO 7
<211> LENGTH: 6707
<212> TYPE: DNA
<213> ORGANISM: Artificial
<220> FEATURE:
<223> OTHER INFORMATION: Synthetic

<400> SEQUENCE: 7

| | | |
|---|---|---|
| tcacaaaaaa taggtacacg aaaaacaagt tacgccccgc cctgccactc atcgcagtac | 60 | |
| tgttgtaatt cattaagcat tctgccgaca tggaagccat cacagacggc atgatgaacc | 120 | |
| tgaatcgcca gcggcatcag caccttgtcg ccttgcgtat aatatttgcc catggtgaaa | 180 | |
| acggggggcga agaagttgtc catattggcc acgtttaaat caaaactggt gaaactcacc | 240 | |

```
cagggattgg ctgagacgaa aaacatattc tcaataaacc ctttagggaa ataggccagg      300
ttttcaccgt aacacgccac atcttgcgaa tatatgtgta gaaactgccg gaaatcgtcg      360
tggtattcac tccagagcga tgaaaacgtt tcagtttgct catggaaaac ggtgtaacaa      420
gggtgaacac tatcccatat caccagctca ccgtctttca ttgccatacg gaattccgga      480
tgagcattca tcaggcgggc aagaatgtga ataaaggccg gataaaactt gtgcttattt      540
ttctttacgg tctttaaaaa ggccgtaata tccagctgaa cggtctggtt ataggtacat      600
tgagcaactg actgaaatgc ctcaaaatgt tctttacgat gccattggga tatatcaacg      660
gtggtatatc cagtgatttt tttctccatt ggtcgtacac tcccttttac tatttaatta      720
tctatgttaa atgattaacg tgctcattta tattttaaca aacttttcac atgaagttaa      780
gttttttaga aaattattta tattttatat tttctcatta tacttctgc tgacttaact       840 ccatccacag ccgctgatat tatgcctcct gcaaatcctg ccccttcacc tgatggatat      900 agtccttta gtgaaatact ttcaagcgac tcatttctag ttatctttaa tggagcggat       960
gttctagtct ctattccagt cattaccgcg tcagagagca tatatcctgt tatttttta     1020 tcaaaattta caagcccctc ttttagtgca gctattacat aaggtggcaa acactctgat    1080
aagctcgcaa atttatatcc tggagtataa atggttttta cgcttcctaa tttactgctt    1140
actgtatcct tcatatataa ccctctttat ttttcctcc ttataaaatt agtataatta     1200
tagcacgagc tctgataaat atgaacatga tgagtgatcg ttaaatttat actgcaatct    1260
gatgcgatta ttgaataaaa gatatgagag atttatctag tttcttttt tacaagaaaa     1320 aagaaagttc ttaaaggttt tatacttttg gtcgtagagc acacggttta acgacttaat    1380
tacgaagtaa ataagtctag tgtgttagac tttaatgttt ttttaaggca ttagtgcatt    1440
taagcgtcag agcatggctt tatgccgaga aaactattgg ttggaatggc gtgtgtgtta    1500
gccaaaggtt tggcgagttg gttggggggtt tcatgggatt aatcccatga aagtaccaac   1560
tcaacaacac actaacgcct gttggttcca accaatagga aattggaata agcaattagt    1620
ataatgagag tataatgttg gtataacgtt agtataatga tgctttttt cattatattt     1680 tttatgtact ttaaacctgc acgcttatgt gaattagaaa aaggttaatc gcatttcata    1740
gattgacctc ccaataacta cgtggtgtta ttgggaggtc aatctatttc atttgcctct    1800
tgctcaaagt tcccaaattc gagtaagagg tatttttgtt tttggtcgtc gcctctcatt    1860
agtagttcag ggtttaacat taatactcca gttttctttt ttataatatt tccttcttct   1920 aagatttaa gtgttgttat tactgttgt agacttgttc ctgtagcttt tgctatttct     1980
cttgttgtag ctatcattgt attgttactt aagtggacat tatctaggat atagttaacg    2040
attttaagtt ttttccgcc aatcatatct aacatactta ttaattgcac tatatatgcc    2100
tttacgaagt taccagacgt tgtttacgg tataacttgt ctacctctat gacttctcca     2160 cttcttcgt ctatgagcct ctgagagcct ttatagactg ttccatatct ttctttcatc    2220
tttttctcac tccttatttt aaactattct aactatatca taactgttct aaaaaaaaaa    2280
gaacatttgt taaagaaat tagaacaaaa tgagtgaaaa attagaacaa acaaattcct     2340
tataaacctt atcatctcaa cctatattaa gatttttacct agttgaatct tcttttctat   2400
ataaagcgtc ggagcatatc agggggttat ctaacgtaaa tgctacccttt cggctcgctt   2460 tcgctcggca ttgacgtcag atactgcacc ccctgaaccc ccatgctcca acagcaaaaa    2520
ggaaactttt tgctgctttt ccgacgctta ttcgcttcgc tcatatttat atagaaagaa    2580
agtgaatgcg caaaagacat aatcgcctga tgcggtattt tctccttacg catctgtgcg    2640
```

```
gtatttcaca ccgcatatgg tgcactctca gtacaatctg ctctgatgcc gcatagttaa    2700
gccagccccg acacccgcca acacccgctg acgcgccctg acgggcttgt ctgctcccgg    2760
catccgctta cagacaagct gtgaccgtct ccgggagctg catgtgtcag aggttttcac    2820
cgtcatcacc gaaacgcgcg agacgaaagg gcctcgtgat acgcctattt ttataggtta    2880
atgtcatgat aataatggtt tcttagacgt caggtggcac ttttcgggga aatgtgcgcg    2940
gaacccctat ttgtttattt ttctaaatac attcaaatat gtatccgctc atgagacaat    3000
aaccctgata aatgcttcaa taatattgaa aaggaagag tatgagtatt caacatttcc    3060
gtgtcgccct tattcccttt tttgcggcat tttgccttcc tgttttgct cacccagaaa    3120 cgctggtgaa agtaaaagat gctgaagatc agttgggtgc acgagtgggt tacatcgaac    3180
tggatctcaa cagcggtaag atccttgaga gttttcgccc cgaagaacgt tttccaatga    3240
tgagcacttt taaagttctg ctatgtggcg cggtattatc ccgtattgac gccgggcaag    3300
agcaactcgg tcgccgcata cactattctc agaatgactt ggttgagtac tcaccagtca    3360
cagaaaagca tcttacggat ggcatgacag taagagaatt atgcagtgct gccataacca    3420
tgagtgataa cactgcggcc aacttacttc tgacaacgat cggaggaccg aaggagctaa    3480 ccgcttttt gcacaacatg ggggatcatg taactcgcct tgatcgttgg gaaccggagc    3540
tgaatgaagc cataccaaac gacgagcgtg acaccacgat gcctgtagca atggcaacaa    3600
cgttgcgcaa actattaact ggcgaactac ttactctagc ttcccggcaa caattaatag    3660
actggatgga ggcggataaa gttgcaggac cacttctgcg ctcggccctt ccggctggct    3720
ggtttattgc tgataaatct ggagccggtg agcgtgggtc tcgcggtatc attgcagcac    3780
tggggccaga tggtaagccc tcccgtatcg tagttatcta cacgacgggg agtcaggcaa    3840
ctatggatga acgaaataga cagatcgctg agataggtgc ctcactgatt aagcattggt    3900
aactgtcaga ccaagtttac tcatatatac tttagattga tttaaaactt catttttaat    3960
ttaaaaggat ctaggtgaag atcctttttg ataatctcat gaccaaaatc ccttaacgtg    4020
agttttcgtt ccactgagcg tcagaccccg tagaaaagat caaaggatct tcttgagatc    4080
ctttttttct gcgcgtaatc tgctgcttgc aaacaaaaa accaccgcta ccagcggtgg    4140
tttgtttgcc ggatcaagag ctaccaactc ttttttccgaa ggtaactggc ttcagcagag    4200
cgcagatacc aaatactgtt cttctagtgt agccgtagtt aggccaccac ttcaagaact    4260
ctgtagcacc gcctacatac ctcgctctgc taatcctgtt accagtggct gctgccagtg    4320
gcgataagtc gtgtcttacc gggttggact caagacgata gttaccggat aaggcgcagc    4380
ggtcgggctg aacggggggt tcgtgcacac agcccagctt ggagcgaacg acctacaccg    4440
aactgagata cctacagcgt gagctatgag aaagcgccac gcttcccgaa gggagaaagg    4500
cggacaggta tccggtaagc ggcagggtcg aacaggaga gcgcacgagg gagcttccag    4560
ggggaaacgc ctggtatctt tatagtcctg tcgggtttcg ccacctctga cttgagcgtc    4620
gatttttgtg atgctcgtca ggggggcgga gcctatggaa aaacgccagc aacgcggcct    4680
ttttacggtt cctggccttt tgctggcctt ttgctcacat gttctttcct gcgttatccc    4740
ctgattctgt ggataaccgt attaccgcct ttgagtgagc tgataccgct cgccgcagcc    4800
gaacgaccga gcgcagcgag tcagtgagcg aggaagcgga agagcgccca atacgcaaac    4860
cgcctctccc cgcgcgttgg ccgattcatt aatgcagctg gcacgacagg tttcccgact    4920
ggaaagcggg cagtgagcgc aacgcaatta atgtgagtta gctcactcat taggcacccc    4980
```

```
aggctttaca ctttatgctt ccggctcgta tgttgtgtgg aattgtgagc ggataacaat    5040
ttcacacagg aaacagctat gaccatgatt acaagcttgc atgcctgcag gtcgactcta    5100
gaggatccac gcgttatatt gataaaaata ataatagtgg gtataattaa gttgttagag    5160
aaaacgtata aattaggagg gattcatatg ccacaatttg gtatattatg taaaacacca    5220
cctaaggtgc ttgttcgtca gtttgtggaa aggtttgaaa gaccttcagg tgagaaaata    5280
gcattatgtg ctgctgaact aacctattta tgttggatga ttacacataa cggaacagca    5340
atcaagagag ccacattcat gagctataat actatcataa gcaattcgct gagtttcgat    5400
attgtcaata aatcactcca gtttaaatac aagacgcaaa aagcaacaat tctggaagcc    5460
tcattaaaga aattgattcc tgcttgggaa tttacaatta ttccttacta tggacaaaaa    5520
catcaatctg atatcactga tattgtaagt agtttgcaat tacagttcga atcatcggaa    5580
gaagcagata agggaaatag ccacagtaaa aaaatgctta aagcacttct aagtgagggt    5640
gaaagcatct gggagatcac tgagaaaata ctaaattcgt ttgagtatac ttcgagattt    5700
acaaaaacaa aaactttata ccaattcctc ttcctagcta ctttcatcaa ttgtggaaga    5760
ttcagcgata ttaagaacgt tgatccgaaa tcatttaaat tagtccaaaa taagtatctg    5820
ggagtaataa tccagtgttt agtgacagag acaaagacaa gcgttagtag gcacatatac    5880
ttctttagcg caaggggtag gatcgatcca cttgtatatt tggatgaatt tttgaggaat    5940
tctgaaccag tcctaaaacg agtaaatagg accggcaatt cttcaagcaa taaacaggaa    6000
taccaattat taaagataa cttagtcaga tcgtacaata aagctttgaa gaaaaatgcg    6060
ccttattcaa tctttgctat aaaaaatggc ccaaaatctc acattggaag acatttgatg    6120
acctcatttc tttcaatgaa gggcctaacg gagttgacta atgttgtggg aaattggagc    6180
gataagcgtg cttctgccgt ggccaggaca acgtatactc atcagataac agcaataccct    6240 gatcactact tcgcactagt ttctcggtac tatgcatatg atccaatatc aaaggaaatg    6300
atagcattga aggatgagac taatccaatt gaggagtggc agcatataga acagctaaag    6360
ggtagtgctg aaggaagcat acgataccc gcatggaatg ggataatatc acaggaggta    6420
ctagactacc tttcatccta cataaataga cgcatataat cgtacagggt agtacaaata    6480
aagaaggcac gtcagatgac gtgcctttt tcttgtgagg atccccggg taccgagctc    6540 gaattcactg gccgtcgttt tacaacgtcg tgactgggaa aaccctggcg ttacccaact    6600
taatcgcctt gcagcacatc ccccttcgc cagctggcgt aatagcgaag aggcccgcac    6660
cgatcgccct tcccaacagt tgcgcagcct gaatggcgaa tggcgat                6707
```

<210> SEQ ID NO 8
<211> LENGTH: 954
<212> TYPE: DNA
<213> ORGANISM: Clostridium Saccharoperbutylacetonicum

<400> SEQUENCE: 8

```
atgattgata gaaaacgtaa aatatctgta ataggagctg gatttgtagg agcaacagca     60
gcttatgctt tgatgaatag tggagtggca acagaaatat gtttatttga tataaatatg    120
gataaagcta tgggagaagt aatggattta gttcatggta catccttgt aaagccagta    180 agtatttatg caggaagtat tgaagaaact aaggattcag atattgtaat aattacagca    240
ggcgcagctc aaaaggaagg ggaaacaaga ttagacttaa ttgaaaaaaa ctataaaata    300
tttaaaagtt ttgttccaca aatagcagcg gcaagtccaa atgcaatttt attagttgta    360
tctaaccctt gtgatgtatt agcatatata acatataaat tatctgggtt ccctaggaa    420
```

```
agagttattg catcaggtac agtgttagat tcatcaagat taaaatatgt cgtaggaaag     480
tattttaatg taaataacaa tgatattcat gcatatgttt taggggagca tggggatagt     540
gaagttgtta gctggagtac agcaagtata gcaggtggaa cattagatga gtatgctgat     600
aaatttgact tagaatggga tgaacaagtg aaggcagtaa ttgaaaatga tgttaaaaat     660
gctgcttatg aaataatatc tagaaagaat gcaacttatt ttgcagtggc attagctgta     720
aacagaatag ttgaagctat tttaagagat gaaaatgcaa ttttaactgt atcatgttta     780
atgcaaggtg agtatggaat tgatgatgta tatcttgcgg taccaacaat tgttaatagc     840
acaggagtta taggaattgt aaatccagtg ataaagatg ctgaagagtt aggaaaatta     900
caagaatcag caaaggtatt aaaggaacac ataaagaaag ttattcctaa ttaa          954
```

<210> SEQ ID NO 9
<211> LENGTH: 10276
<212> TYPE: DNA
<213> ORGANISM: Artificial
<220> FEATURE:
<223> OTHER INFORMATION: Synthetic

<400> SEQUENCE: 9

```
tcacaaaaaa taggtacacg aaaaacaagt tacgccccgc cctgccactc atcgcagtac      60
tgttgtaatt cattaagcat tctgccgaca tggaagccat cacagacggc atgatgaacc     120
tgaatcgcca gcggcatcag caccttgtcg ccttgcgtat aatatttgcc catggtgaaa     180 acggggcga agaagttgtc catattggcc acgtttaaat caaaactggt gaaactcacc     240
cagggattgg ctgagacgaa aaacatattc tcaataaacc ctttagggaa ataggccagg     300
ttttcaccgt aacacgccac atcttgcgaa tatatgtgta gaaactgccg gaaatcgtcg     360
tggtattcac tccagagcga tgaaaacgtt tcagtttgct catggaaaac ggtgtaacaa     420
gggtgaacac tatcccatat caccagctca ccgtctttca ttgccatacg gaattccgga     480
tgagcattca tcaggcgggc aagaatgtga ataaaggccg gataaaactt gtgcttattt     540
ttctttacgg tctttaaaaa ggccgtaata tccagctgaa cggtctggtt ataggtacat     600
tgagcaactg actgaaatgc ctcaaaatgt tctttacgat gccattggga tatatcaacg     660
gtggtatatc cagtgatttt tttctccatt ggtcgtacac tccctttac tatttaatta     720 tctatgttaa atgattaacg tgctcattta tattttaaca aacttttcac atgaagttaa     780
gttttttaga aaattattta tattttatat tttctcatta tactttctgc tgacttaact     840
ccatccacag ccgctgatat tatgcctcct gcaaatcctg ccccttcacc tgatggatat     900
agtcctttta gtgaaatact ttcaagcgac tcatttctag ttatctttaa tggagcggat     960
gttctagtct ctattccagt cattaccgcg tcagagagca tatatcctgt tattttttta    1020
tcaaaattta caagcccctc ttttagtgca gctattacat aaggtggcaa acactctgat    1080
aagctcgcaa atttatatcc tggagtataa gatggtttta cgcttcctaa tttactgctt    1140
actgtatcct tcatatataa ccctctttat tttttcctcc ttataaaatt agtataatta    1200
tagcacgagc tctgataaat atgaacatga tgagtgatcg ttaaatttat actgcaatct    1260
gatgcgatta ttgaataaaa gatatgagag atttatctag tttctttttt tacaagaaaa    1320 agaaagttc ttaaaggttt tatacttttg gtcgtagagc acacggttta acgacttaat    1380
tacgaagtaa ataagtctag tgtgttagac tttaatgttt ttttaaggca ttagtgcatt    1440
taagcgtcag agcatggctt tatgccgaga aaactattgg ttggaatggc gtgtgtgtta    1500
```

```
gccaaaggtt aatcgcattt catagattga cctcccaata actacgtggt gttattggga    1560
ggtcaatcta tttcatttgc ctcttgctca aagttcccaa attcgagtaa gaggtatttt    1620 tgttttggt cgtcgcctct cattagtagt tcagggttta acattaatac tccagttttt    1680
ctttttataa tatttccttc ttctaagatt ttaagtgttg ttattactgt ttgtagactt    1740
gttcctgtag cttttgctat ttctcttgtt gtagctatca ttgtattgtt acttaagtgg    1800
acattatcta ggatatagtt aacgatttta agttttttc cgccaatcat atctaacata    1860
cttattaatt gcactatata tgcctttacg aagttaccag acgtttgttt acggtataac    1920
ttgtctacct ctatgacttc tccactttct tcgtctatga gcctctgaga gcctttatag    1980
actgttccat atctttcttt catctttttc tcactcctta ttttaaacta ttctaactat    2040
atcataactg ttctaaaaaa aaagaacat ttgttaaaag aaattagaac aaaatgagtg    2100
aaaaattaga acaaacaaat tccttataaa ccttatcatc tcaacctata ttaagatttt    2160
acctagttga atcttctttt ctatataaag cgtcggagca tatcagggggg ttatctaacg    2220 taaatgctac ccttcggctc gctttcgctc ggcattgacg tcagatactg cacccctga    2280 accccatgc tccaacagca aaaggaaac ttttgctgc ttttccgacg cttattcgct    2340
tcgctcatat ttatatagaa aagaagtgaa tgcgcaaaag acataatcgc ctgatgcggt    2400
attttctcct tacgcatctg tgcggtattt cacaccgcat atggtgcact ctcagtacaa    2460
tctgctctga tgccgcatag ttaagccagc ccgacaccc gccaacaccc gctgacgcgc    2520
cctgacgggc ttgtctgctc ccggcatccg cttacagaca gctgtgacc gtctccggga    2580 gctgcatgtg tcagaggttt tcaccgtcat caccgaaacg cgcgagacga aagggcctcg    2640
tgatacgcct attttataq gttaatgtca tgataataat ggtttcttag acgtcaggtg    2700
gcacttttcg gggaaatgtg cgcggaaccc ctatttgttt attttctaa atacattcaa    2760 atatgtatcc gctcatgaga caataaccct gataaatgct tcaataatat tgaaaagga    2820 agagtatgag tattcaacat ttccgtgtcg cccttattcc cttttttgcg cattttgcc    2880 ttcctgtttt tgctcaccca gaaacgctgg tgaaagtaaa agatgctgaa gatcagttgg    2940
gtgcacgagt gggttacatc gaactggatc tcaacagcgg taagatcctt gagagttttc    3000
gccccgaaga acgttttcca atgatgagca cttttaaagt tctgctatgt ggcgcggtat    3060
tatcccgtat tgacgccggg caagagcaac tcggtcgccg catacactat tctcagaatg    3120
acttggttga gtactcacca gtcacagaaa agcatcttac ggatggcatg acagtaagag    3180
aattatgcag tgctgccata accatgagtg ataacactgc ggccaactta cttctgacaa    3240
cgatcggagg accgaaggag ctaaccgctt ttttgcacaa catgggggat catgtaactc    3300
gccttgatcg ttgggaaccg gagctgaatg aagccatacc aaacgacgag cgtgacacca    3360
cgatgcctgt agcaatggca acaacgttgc gcaaactatt aactggcgaa ctacttactc    3420
tagcttcccg gcaacaatta atagactgga tggaggcgga taaagttgca ggaccacttc    3480
tgcgctcggc ccttccggct ggctggttta ttgctgataa atctggagcc ggtgagcgtg    3540
ggtctcgcgg tatcattgca gcactggggc cagatggtaa gccctcccgt atcgtagtta    3600
tctacacgac ggggagtcag gcaactatgg atgaacgaaa tagacagatc gctgagatag    3660
gtgcctcact gattaagcat tggtaactgt cagaccaagt ttactcatat atactttaga    3720
ttgatttaaa acttcatttt taatttaaaa ggatctaggt gaagatcctt tttgataatc    3780
tcatgaccaa aatcccttaa cgtgagtttt cgttccactg agcgtcagac cccgtagaaa    3840
agatcaaagg atcttcttga gatccttttt ttctgcgcgt aatctgctgc ttgcaaacaa    3900
```

```
aaaaaccacc gctaccagcg gtggtttgtt tgccggatca agagctacca actcttttc     3960
cgaaggtaac tggcttcagc agagcgcaga taccaaatac tgttcttcta gtgtagccgt    4020
agttaggcca ccacttcaag aactctgtag caccgcctac atacctcgct ctgctaatcc    4080
tgttaccagt ggctgctgcc agtggcgata agtcgtgtct taccggggttg gactcaagac   4140
gatagttacc ggataaggcg cagcggtcgg gctgaacggg gggttcgtgc acacagccca    4200
gcttggagcg aacgacctac accgaactga gatacctaca gcgtgagcta tgagaaagcg    4260
ccacgcttcc cgaagggaga aaggcggaca ggtatccggt aagcggcagg gtcggaacag    4320
gagagcgcac gagggagctt ccaggggaa acgcctggta tctttatagt cctgtcgggt     4380
ttcgccacct ctgacttgag cgtcgatttt tgtgatgctc gtcaggggg cggagcctat     4440
ggaaaaacgc cagcaacgcg ccttttttac ggttcctggc cttttgctgg ccttttgctc    4500
acatgttctt tcctgcgtta tcccctgatt ctgtggataa ccgtattacc gcctttgagt    4560
gagctgatac cgctcgccgc agccgaacga ccgagcgcag cgagtcagtg agcgaggaag    4620
cggaagagcg cccaatacgc aaaccgcctc tccccgcgcg ttggccgatt cattaatgca    4680
gctggcacga caggttttcc cgactggaaag cgggcagtga gcgcaacgca attaatgtga   4740
gttagctcac tcattaggca ccccaggctt tacactttat gcttccggct cgtatgttgt    4800
gtggaattgt gagcggataa caatttcaca caggaaacag ctatgaccat gattacgccg    4860
ataaaaagat aaaagggtat gcacgtgaag atgcagtatt gacaggaata gaaactagaa    4920
cctcagcacc agtaacgctt aatagggatt ctaaggttga aagcgtaaat gttagtggac    4980
tttatccaac aggagaaggc gctggctttg caggtggaat aatatcagct gcagttgatg    5040
gtataaaagt tgctgaacat ataatcgaaa aatttgcttt accaaaagaa atataagata    5100
tatttatgtg agtttgaaaa ataccagaga aatctggtat ttttttatatc aaaaatacat   5160
taaattatta aatttgttaa atttttattt aaatttaaaa ataattttct gaaaatttag    5220
catttgtact tatttttttgt tacaatagaa aaagggatta taataaccat gattgatata    5280
aatttaacaa atattaacc ttatattaaa taaataaaaa aataattatt aagtaagagg     5340
tgcaagaaaa gcttataatt atccttagat atccatgcag tgcgcccaga tagggtgtta    5400
agtcaagtag tttaaggtac tactctgtaa gataacacag aaaacagcca acctaaccga    5460
aaagcgaaag ctgatacggg aacagagcac ggttggaaag cgatgagtta cctaaagaca    5520
atcgggtacg actgagtcgc aatgttaatc agatataagg tataagttgt gtttactgaa    5580
cgcaagtttc taatttcgat tatatctcga tagaggaaag tgtctgaaac ctctagtaca    5640
aagaaaggta agttatatgc atggacttat ctgttatcac cacatttgta caatctgtag    5700
gagaacctat gggaacgaaa cgaaagcgat gccgagaatc tgaatttacc aagacttaac    5760
actaactggg gataccctaa acaagaatgc ctaatagaaa ggaggaaaaa ggctatagca    5820
ctagagcttg aaaatcttgc aagggtacgg agtactcgta gtagtctgag aagggtaacg    5880
cccttaccat ggcaaagggg tacagttatt gtgtactaaa attaaaaatt gattagggag    5940
gaaaacctca aaatgaaacc aacaatggca attttagaaa gaatcagtaa aaattcacaa    6000
gaaaatatag acgaagtttt tacaagactt tatcgttatc ttttacgtcc agatatttat    6060
tacgtggcga cgcgtgaagt tcctatactt tctagagaat aggaacttcg cgactcatag    6120
aattatttcc tcccgttaaa taatagataa ctattaaaaa tagacaatac ttgctcataa    6180
gtaacggtac ttaaattgtt tactttggcg tgtttcattg cttgatgaaa ctgattttta    6240
```

```
gtaaacagtt gacgatattc tcgattgacc cattttgaaa caaagtacgt atatagcttc    6300
caatatttat ctggaacatc tgtggtatgg cgggtaagtt ttattaagac actgtttact    6360
tttggtttag gatgaaagca ttccgctggc agcttaagca attgctgaat cgagacttga    6420
gtgtgcaaga gcaaccctag tgttcggtga atatccaagg tacgcttgta gaatccttct    6480
tcaacaatca gatagatgtc agacgcatgg cttttcaaaaa ccactttttt aataatttgt    6540
gtgcttaaat ggtaaggaat actcccaaca attttatacc tctgtttgtt agggaattga    6600
aactgtagaa tatcttggtg aattaaagtg acacgagtat tcagttttaa ttttttctgac    6660
gataagttga atagatgact gtctaattca atagacgtta cctgtttact tattttagcc    6720
agtttcgtcg ttaaatgccc tttacctgtt ccaatttcgt aaacggtatc ggtttctttt    6780
aaattcaatt gtttttattat ttggttgagt acttttttcac tcgttaaaaa gttttgagaa    6840
tattttatat ttttgttcat accagcacca gaagcaccag catctcttgg gttaattgag    6900
gcctgagtat aaggtgactt atacttgtaa tctatctaaa cggggaaccct ctctagtaga    6960
caatcccgtg ctaaattgta ggactgccct ttaataaata cttctatatt taagaggta    7020
tttatgaaaa gcggaattta tcagattaaa aatactttct ctagagaaaa tttcgtctgg    7080
attagttact tatcgtgtaa aatctgataa atggaattgg ttctacataa atgcctaacg    7140
actatccctt tggggagtag ggtcaagtga ctcgaaacga tagacaactt gctttaacaa    7200
gttggagata tagtctgctc tgcatggtga catgcagctg gatataattc cggggtaaga    7260
ttaacgacct tatctgaaca taatgccata tgaatccctc ctaatttata cgttttctct    7320
aacaacttaa ttatacccac tattattatt tttatcaata tagaagttcc tatactttct    7380
agagaatagg aacttcacgc gttgggaaat ggcaatgata gcgaaacaac gtaaaactct    7440
tgttgtatgc tttcattgtc atcgtcacgt gattcataaa cacaagtgaa tgtcgacagt    7500
gaattttttac gaacgaacaa taacagagcc gtatactccg agagggtac gtacggttcc    7560
cgaagagggt ggtgcaaacc agtcacagta atgtgaacaa ggcggtacct ccctacttca    7620
ccatatcatt ttctgcagcc ccctagaaat aatttttgttt aactttaaga aggagatata    7680
catatatggc tagatcgtcc attccgacag catccgccagt cactatggcg tgctgctagc    7740
gctatatgcg ttgatgcaat ttctatgcac tcgtagtagt ctgagaaggg taacgccctt    7800
tacatggcaa agggggtacag ttattgtgta ctaaaattaa aaattgatta gggaggaaaa    7860
cctcaaaatg aaaccaacaa tggcaatttt agaaagaatc agtaaaaatt cacaagaaaa    7920
tatagacgaa gttttttacaa gactttatcg ttatcttttta cgtccagata tttattacgt    7980
ggcgtatcaa aatttatatt ccaataaagg agcttccaca aaaggaatat tagatgatac    8040
agcggatggc tttagtgaag aaaaaaataaa aaagattatt caatctttaa aagacggaac    8100
ttactatcct caacctgtac gaagaatgta tattgcaaaa aagaattcta aaaagatgag    8160
acctttagga attccaactt tcacagataa attgatccaa gaagctgtga gaataattct    8220
tgaatctatc tatgaaccgg tattcgaaga tgtgtctcac ggttttagac ctcaacgaag    8280
ctgtcacaca gctttgaaaa caatcaaaag agagtttggc ggcgcaagat ggtttgtgga    8340
gggagatata aaaggctgct tcgataatat agaccacgtt acactcattg gactcatcaa    8400
tcttaaaatc aaagatatga aaatgagcca attgatttat aaatttctaa aagcaggtta    8460
tctggaaaac tggcagtatc acaaaactta cagcggaaca cctcaaggtg gaattctatc    8520
tcctcttttg gccaacatct atcttcatga attggataag tttgtttttac aactcaaaat    8580
gaagtttgac cgagaaagtc cagaaagaat aacacctgaa tatcgggagc tccacaatga    8640
```

```
gataaaaaga atttctcacc gtctcaagaa gttggagggt gaagaaaaag ctaaagttct    8700
tttagaatat caagaaaaac gtaaaagatt acccacactc ccctgtacct cacagacaaa    8760
taaagtattg aaatacgtcc ggtatgcgga cgacttcatt atctctgtta aaggaagcaa    8820
agaggactgt caatggataa aagaacaatt aaaactttt attcataaca agctaaaaat     8880
ggaattgagt gaagaaaaaa cactcatcac acatagcagt caacccgctc gttttctggg    8940
atatgatata cgagtaagga gatctggaac gataaaacga tctggtaaag tcaaaaagag    9000
aacactcaat gggagtgtag aactccttat tcctcttcaa gacaaaattc gtcaatttat    9060
ttttgacaag aaaatagcta tccaaaagaa agatagctca tggtttccag ttcacaggaa    9120
atatcttatt cgttcaacag acttagaaat catcacaatt tataattctg aactccgcgg    9180
gatttgtaat tactacggtc tagcaagtaa ttttaaccag ctcaattatt ttgcttatct    9240
tatggaatac agctgtctaa aaacgatagc ctccaaacat aagggaacac tttcaaaaac    9300
catttccatg tttaaagatg gaagtggttc gtggggatc ccgtatgaga taaagcaagg     9360
taagcagcgc cgttattttg caaattttag tgaatgtaaa tccccttatc aatttacgga    9420
tgagataagt caagctcctg tattgtatgg ctatgcccgg aatactcttg aaaacaggtt    9480
aaaagctaaa tgttgtgaat tatgtgggac gtctgatgaa aatacttcct atgaaattca    9540
ccatgtcaat aaggtcaaaa atcttaaagg caaagaaaaa tgggaaatgg caatgatagc    9600
gaaacaacgt aaaactcttg ttgtatgctt tcattgtcat cgtcacgtga ttcataaaca    9660
caagtgaatg tcgagcaccc gttctcggag cactgtccga ccgctttggc cgccgcccag    9720
tcctgctcgc ttcgctactt ggagccacta tcgactacgc gatcatggcg accacacccg    9780
tcctgtggat cgccaagctc gccgatggta gtgtggggtc tccccatgcg agagtaggga    9840
actgccaggc atcaaataaa acgaaaggct cagtcgaaag actgggcctt tcgttttatc    9900
tgttgtttgt cggtgaacgc tctcctgagt aggacaaatc cgccgggagc ggatttgaac    9960
gttgcgaagc aacggcccgg agggtggcgg gcaggacgcc cgccataaac tgccaggcat   10020
caaattaagc agaaggccat cctgacggat ggccttttg cgtttctaca aactcttcct    10080
gtcgtcatat ctacccgggt accgagctcg aattcactgg ccgtcgtttt acaacgtcgt   10140
gactgggaaa accctggcgt tacccaactt aatcgccttg cagcacatcc ccctttcgcc   10200
agctggcgta atagcgaaga ggcccgcacc gatcgccctt cccaacagtt gcgcagcctg   10260
aatggcgaat ggcgat                                                   10276
```